(12) United States Patent
Hu et al.

(10) Patent No.: US 9,013,692 B2
(45) Date of Patent: Apr. 21, 2015

(54) FLOW CYTOMETER APPARATUS FOR THREE DIMENSIONAL DIFRACTION IMAGING AND RELATED METHODS

(75) Inventors: Xin-Hua Hu, Greenville, NC (US); Kenneth M. Jacobs, Greenville, NC (US); Jun O. Lu, Greenville, NC (US)

(73) Assignee: East Carolina University, Greenville, NC (US)

( * ) Notice: Subject to any disclaimer, the term of this patent is extended or adjusted under 35 U.S.C. 154(b) by 1164 days.

(21) Appl. No.: 12/997,186

(22) PCT Filed: Jun. 11, 2009

(86) PCT No.: PCT/US2009/003508
§ 371 (c)(1),
(2), (4) Date: Dec. 9, 2010

(87) PCT Pub. No.: WO2009/151610
PCT Pub. Date: Dec. 17, 2009

(65) Prior Publication Data
US 2011/0090500 A1  Apr. 21, 2011

Related U.S. Application Data

(60) Provisional application No. 61/060,993, filed on Jun. 12, 2008.

(51) Int. Cl.
*G01N 21/00* (2006.01)
*G01N 15/14* (2006.01)
*G01N 15/02* (2006.01)

(52) U.S. Cl.
CPC ........ *G01N 15/1475* (2013.01); *G01N 15/0211* (2013.01); *G01N 15/147* (2013.01); *G01N 2015/0222* (2013.01); *G01N 2015/025* (2013.01); *G01N 2015/1497* (2013.01)

(58) Field of Classification Search
CPC .................................................. G01N 21/00
USPC ............ 356/335–337, 281; 250/459.1, 461.2, 250/573, 574
See application file for complete search history.

(56) References Cited

U.S. PATENT DOCUMENTS 3,960,449 A  6/1976  Carleton et al.
4,293,221 A  10/1981  Kay et al.
(Continued)

FOREIGN PATENT DOCUMENTS

CN    1511299 A    7/2004
CN    1685226 A    10/2005
(Continued)

OTHER PUBLICATIONS

Chen, C. et al., "Numerical study of reflectance imaging using a parallel Monte Carlo Method", Med. Phys 2007, vol. 34, No. 7 pp. 2939-2948, Jul. 31, 2007.
(Continued)

*Primary Examiner* — Kara E Geisel
*Assistant Examiner* — Iyabo S Alli
(74) *Attorney, Agent, or Firm* — Myers Bigel Sibley & Sajovec, PA

(57) ABSTRACT

A flow cytometer assembly includes a fluid controller configured to form a hydrodynamically focused flow stream including an outer sheath fluid and an inner core fluid. A coherent light source is configured to illuminate a particle in the inner core fluid. A detector is configured to detect a spatially coherent distribution of elastically scattered light from the particle excited by the coherent light source. An analyzing module configured to extract a three-dimensional morphology parameter of the particle from a spatially coherent distribution of the elastically scattered light.

37 Claims, 14 Drawing Sheets

(56) References Cited

U.S. PATENT DOCUMENTS

| | | | |
|---|---|---|---|
| 4,500,641 | A | 2/1985 | Van den Engh et al. |
| 5,017,497 | A | 5/1991 | De Grooth et al. |
| 5,308,990 | A | 5/1994 | Takahashi et al. |
| 5,416,582 | A | 5/1995 | Knutson |
| 5,929,443 | A | 7/1999 | Alpano |
| 7,127,109 | B1 | 10/2006 | Kim et al. |
| 8,120,770 | B2 * | 2/2012 | Huang et al. ............ 356/246 |
| 8,520,205 | B2 * | 8/2013 | Silcott ..................... 356/336 |
| 2002/0141625 | A1 | 10/2002 | Nelson |
| 2005/0110996 | A1 | 5/2005 | Sharpe et al. |
| 2007/0133002 | A1 | 6/2007 | Wax et al. |

FOREIGN PATENT DOCUMENTS

| | | |
|---|---|---|
| EP | 0 061 809 | 10/1982 |
| EP | 1707944 A2 | 10/2006 |
| WO | WO 98/34094 | 8/1998 |
| WO | WO 2004/017041 A2 | 2/2004 |
| WO | WO 2010/039921 | 4/2010 |

OTHER PUBLICATIONS

Chen, C. et al., "A primary method for determination of optical parameters of turbid samples and application to intralipid between 550 and 1630nm", Optics Express 2006, vol. 14. No. 16, pp. 7420-7435, Aug. 7, 2006.

Yuan Cao-Jin et al; "Three-dimensional surface contouring of reflecting micro-object by digital holography with short-coherence light source"; Acta Physica Sinica vol. 56, No. 1, Jan. 2007 Chin. Phys. Soc. pp. 218-223.

International Search Report and Written Opinion for PCT/US2009/059174, mailed May 10, 2010, 11 pages.

International Preliminary Report on Patentability for PCT/US2009/059174, mailed Apr. 14, 2011, 6 pages.

International Search Report and Written Opinion for PCT/US2009/003508, mailed Jan. 19, 2010, 11 pages.

International Preliminary Report on Patentability for PCT/US2009/003508, mailed Dec. 23, 2010.

* cited by examiner

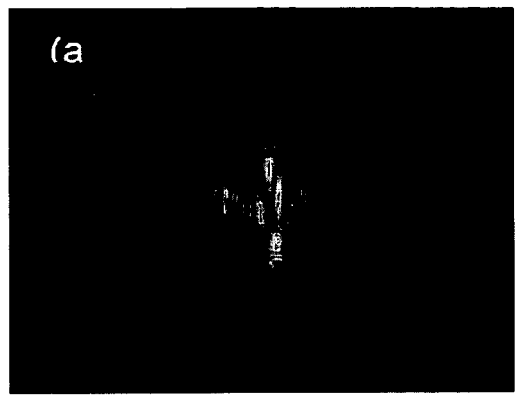
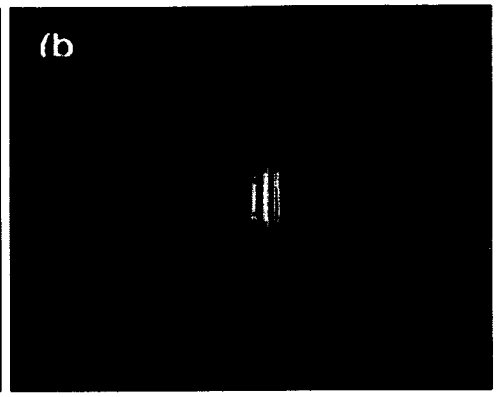
FIGURE 8A          FIGURE 8B
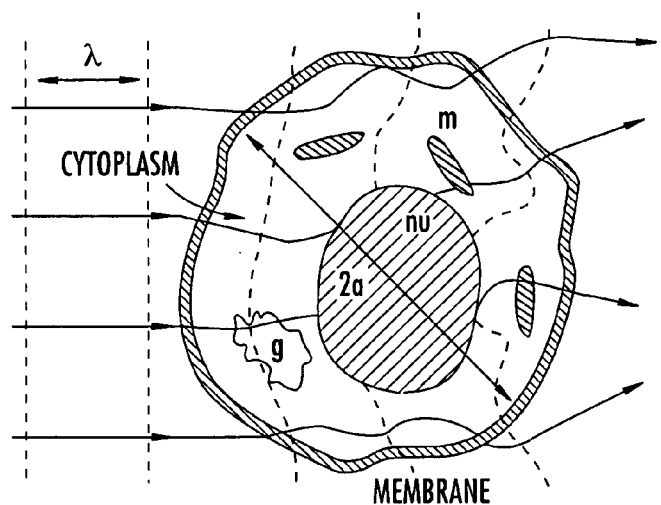
FIG. 9

TABLE 2     THE 3D STRUCTURE PARAMETERS OF 7 NALM-6 CELLS

| | CLASS 1 SMALL CELL SIZE | | CLASS 2 LARGE CELL SIZE | | | CLASS 3 SPLITTING NUCLEUS | |
|---|---|---|---|---|---|---|---|
| CELL LABEL | #1 | #3 | #7 | #2 | #8 | #10 | #9 |
| IMAGE* | | | | | | | |
| $V_c (\mu m^3)$* | 445 | 492 | 523 | 539 | 566 | 628 | 736 |
| N/C RATIO* | 0.549 | 0.549 | 0.524 | 0.556 | 0.526 | 0.547 | 0.507 |

* IMAGES ARE NOT SCALED TO EACH OTHER, $V_c$ = CELL VOLUME, N/C RATIO = NUCLEAR VOLUME $V_n$ / CELL VOLUME $V_c$

FIG. 10

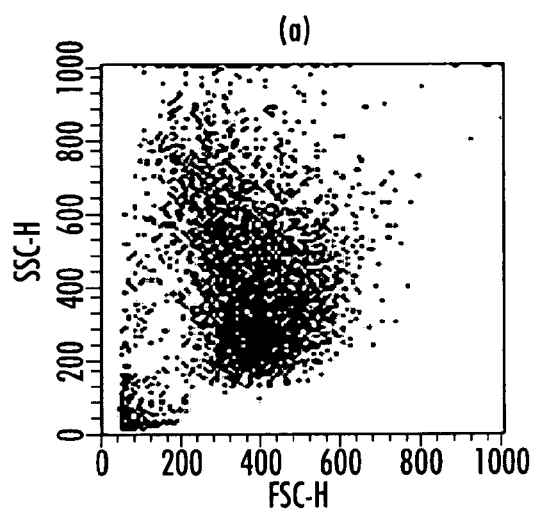
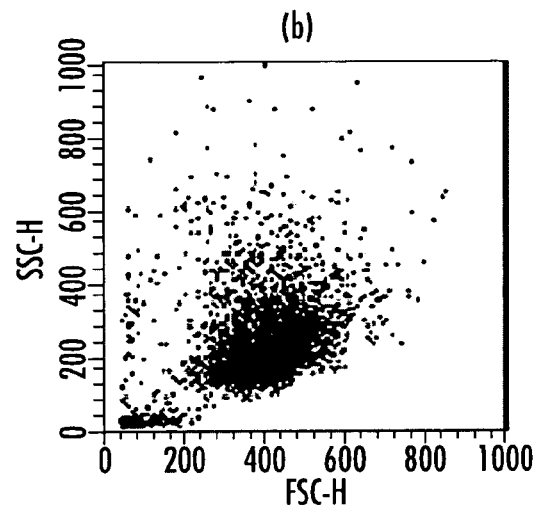
FIG. 17A  FIG. 17B
FIG. 18

9.6μm DIAMETER SPHERES IN 532nm LIGHT, FLOW SPEED: 1.6mm/s~1.8mm/s, 50μs 9.6μm DIAMETER SPHERES IN 532nm LIGHT, FLOW SPEED: 12mm/s, 50μs exposure 5.2μm DIAMETER, 4.7mm/s 9.6μm DIAMETER, 12mm/s 25μm DIAMETER, 7mm/s

FLOW CYTOMETER APPARATUS FOR THREE DIMENSIONAL DIFRACTION IMAGING AND RELATED METHODS

RELATED APPLICATIONS

This application is a 35 U.S.C. §371 national phase application of PCT Application PCT/US 2009/003508, filed Jun. 11, 2009, and published on Dec. 17, 2009, as International Publication No. WO 2009/151610 A2, and which claims the benefit under 35 U.S.C. §119(e) of U.S. Provisional Patent Application Ser. No. 61/060,993, filed Jun. 12, 2008, the disclosure of each of which is incorporated herein by reference in its entirety.

FIELD OF THE INVENTION

The present invention relates to flow cytometers, and in particular to flow cytometers for detection of three dimensional morphology parameters and imaging.

BACKGROUND

Flow cytometers are used in life science research for quantitative assays of large populations of biological cells and particles. A beam of light (typically of a single wavelength) is directed onto a hydrodynamically focused stream of fluid. The fluid stream typically includes a fluid carrier or "sheath" and a core fluid including a plurality of particles. The fluid stream generally permits one particle to pass through the light beam at a time. A number of detectors can be aimed at the point where the stream passes through the light beam. For example, a detector can be positioned in line with the light beam to detect forward scatter and one or more detectors can be positioned perpendicular to the light beam to detect side scatter. The particles can contain fluorescent components, and one or more fluorescent detectors can be used to detect a resulting fluorescence signal. Each suspended particle passing through the light beam scatters the light in some way and/or a fluorescent component on the particle may fluoresce light, e.g., at a lower frequency than the light source. Scattered and fluorescent light can be detected and analyzed.

The signals detected from a flow cytometer can be used to characterize the physical and/or chemical structure of the particles. For example, the forward scattered light can be correlated with a cell volume, and the side scattered light may be correlated with the shape or other inner features of the particle. The scattered and/or fluorescence signals are acquired by detectors that allow fast signal acquisition (e.g., thousands of cells per second) and rapid data analysis for a large cell population. For example, the cells can be classified in a multi-dimensional feature space defined by various fluorescence signals, forward scatter signals, and/or side scatter signals.

More recently, imaging flow cytometers are available in which a CCD camera is used to record bright-field, dark field, and fluorescent images. These imaging flow cytometers use microscope techniques to acquire two dimensional images from each interrogated cell for analysis of features at a rate of up to about 100 cells per second. However, these techniques rely on conventional fluorescence or bright-field microscopy in which the resulting images are non-diffractional and inherently two dimensional replicas of the three dimensional cell structure (with the third dimension being compressed into a "focal depth"). Although these two dimensional images can be analyzed with pattern recognition algorithms, automated analysis with existing pattern recognition algorithms is complex, labor intensive, and challenging at least because of the two dimensional nature of the image.

Confocal imaging techniques have been used in non-flow applications to acquire multiple two dimensional non-diffraction images of very short focal depth and stack them along the third dimension to provide a three dimensional construction. However, this technique typically requires multiple images and, therefore, these confocal imaging techniques are generally not compatible with an imaging flow cytometer in which the particles are moving relatively rapidly.

In addition, the high flow speeds and poor signal to noise ratios in conventional flow cytometers may limit the amount of information that can be extracted from the scattering and/or fluorescence signals.

SUMMARY OF EMBODIMENTS OF THE INVENTION

According to embodiments of the present invention, a flow cytometer assembly includes a fluid controller configured to form a hydrodynamically focused flow stream including an outer sheath fluid and an inner core fluid. A coherent light source is configured to illuminate a particle in the inner core fluid. A detector is configured to detect a spatially coherent distribution of elastically scattered light from the particle excited by the coherent light source. An analyzing module configured to extract a three-dimensional morphology parameter of the particle from a spatially coherent distribution of the elastically scattered light.

According to some embodiments of the invention, the detector is further configured to provide diffraction image data of the particle comprising the spatially coherent distribution of the elastically scattered light.

In particular embodiments, a non-coherent light source is configured to illuminate the particle and a detector is configured to detect non-coherent image data comprising bright-field and/or dark-field and/or fluorescence signals from the particle excited by the non-coherent light source. The analyzing module can be configured to combine the diffraction image data and the non-coherent image data for a particle in the core fluid.

In some embodiments, the analyzing module is configured to classify the particles based on the coherence distribution of the elastically scattered light. The analyzing module can be configured to extract a volume of a structure of the particle based on the diffraction image data, such as a volume of the cytoplasm and/or nucleus and/or mitochondrion in a biological cell.

In some embodiments, the fluid controller is configured to form a laminar flow stream. The fluid controller can include a flow cell having an index of refraction that is substantially similar to an index of refraction of the fluid sheath. The flow cell can have at least one generally planar side.

In some embodiments, the detector is configured to detect light scattered within an angle range centered at an angle offset from a direction of light propagation from the coherent light source, such as at about 90 degrees.

In some embodiments, the three-dimensional morphology parameters are extracted based on a database of calculated diffraction image data and/or experimentally determined cell structures.

According to further embodiments of the present invention, methods of analyzing particles in a flow cytometer to determine three-dimensional morphology parameters include forming a hydrodynamically focused flow stream including an outer sheath fluid and an inner core fluid. A particle in the inner core fluid is illuminated with a coherent light source. Elastically scattered light is detected from the particle that is excited by the coherent light source. A three-dimensional morphology parameter of the particle is extracted from a spatially coherent distribution of the elastically scattered light.

According to further embodiments of the present invention, computer program products for analyzing particles in a flow cytometer to determine three-dimensional morphology parameters are provided. The flow cytometer has a hydrodynamically focused flow stream including an outer sheath fluid and an inner core fluid, a coherent light source configured to illuminate a particle, and a detector for detecting a coherent distribution of elastically scattered light from the particle excited by the coherent light source. The computer program product includes a computer usable storage medium having computer-readable program code embodied in the medium. The computer-readable program code is configured to receive diffraction image data comprising a spatially coherent distribution of elastically scattered light from the flow cytometer. Computer-readable program code is configured to extract three-dimensional morphology parameters of the particle from the spatially coherent distribution of the elastically scattered light.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 8a is a diffraction image from a 25 µm microsphere flown in the core fluid excited by a 633 m laser.

FIG. 8b is a Mie theory-calculated diffraction image with horizontal axis as $\theta_s$ and vertical as $\phi_s$ between 70° and 110° and no adjustable parameters.

FIG. 9 is a schematic representation of the incident and scattered wavefronts by a biological cell with inhomogeneous distribution of refraction index, where nu=nucleus, m=mitochondria, g=Golgi apparatus, λ=wavelength, and 2a=size.

FIG. 10 is a table including the three dimensional structural parameters of seven NALM-6 cells.

FIGS. 17A-17B are graphs illustrating scatter plots of side scatter channel (SSC) versus forward scatter channel (FSC) obtained from 10,000 of B16/GPR4 cells (FIG. 17A) and B16/vector (FIG. 17B), respectively.

FIG. 18 is an image of two cross-sectional views of the three-dimensional structure of a B16/GPR4 cell.

DETAILED DESCRIPTION OF EMBODIMENTS OF THE INVENTION

Figure 1:
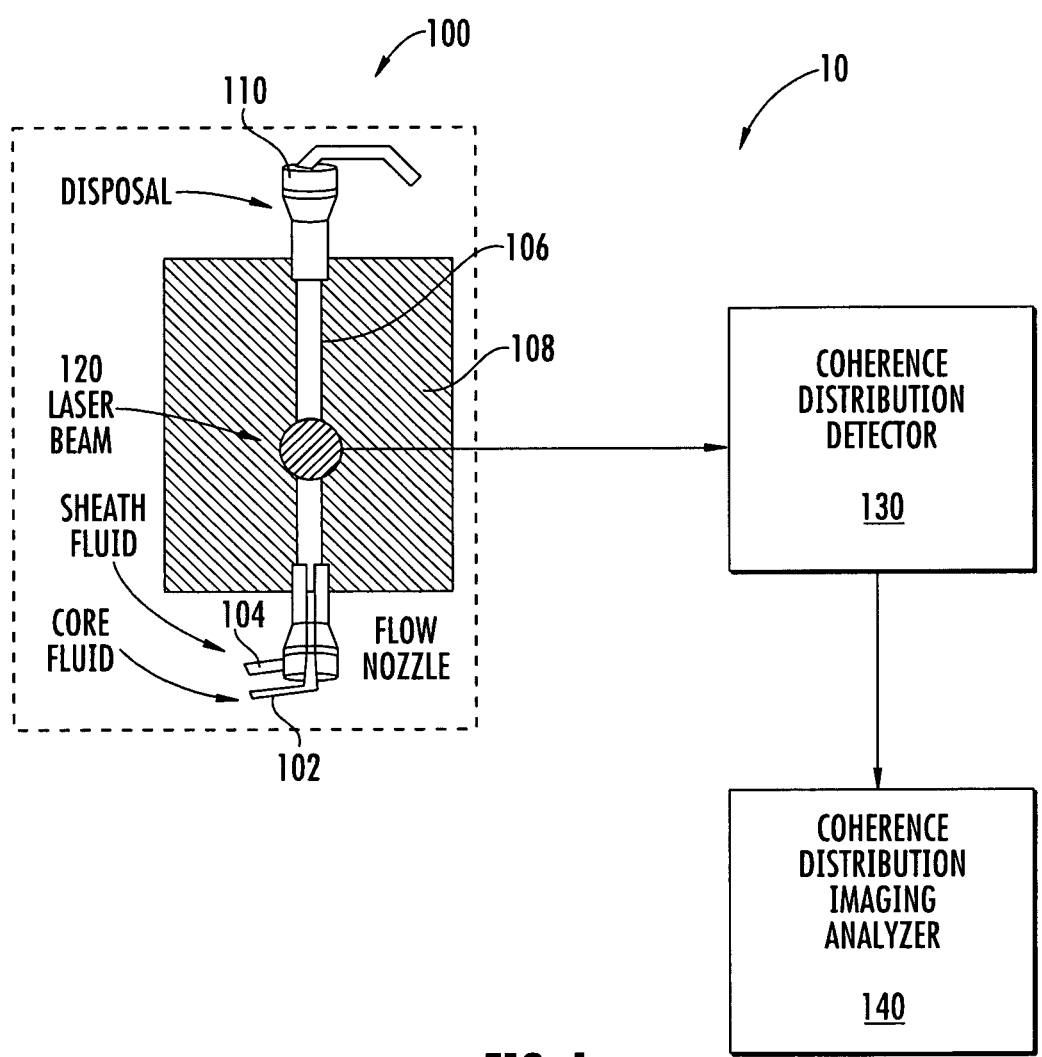
FIG. 1 is a schematic diagram of a cytometer assembly according to embodiments of the present invention.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, embodiments of the present invention may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

"Imaging data" is a spatial distribution of signals, e.g., recorded by an imaging detector. Accordingly, optical images are spatial distributions of electromagnetic fields comprising the optical waves of light and can be generally divided into two categories: 1) a "diffraction" image that is based on the spatially coherent distribution of light signals, and 2) a "non-diffraction" image that is based on the non-coherent distribution of light signals. The feature that separate these two types of imaging data lie in the existence of the coherence among the electromagnetic fields at different spatial locations. Diffraction images are acquired from light signals that are dominated by highly coherent fields at different locations while non-diffraction images are acquired from light signals that are dominated by fields of little coherence at different locations. Conventional optical microscopy, for example, is a widely used tool to acquire non-diffraction (or diffraction limited) images of either bright-field of elastically scattered light or of fluorescence light signals from particles excited with a non-coherent light source; however, the images are non-diffractional and inherently two-dimensional replica of the three-dimensional cell structures in real space with the $3^{rd}$ dimension compressed into a "focal depth." In comparison, diffraction images can be acquired from a particle illuminated or excited with a coherent light source such as a laser and used to extract three-dimensional morphology parameters about the particle. One example of a diffraction image is a hologram which is made by the recording of the interference between the elastically scattered light from an object illuminated with a laser beam and a reference beam split off the laser beam. The hologram can be illuminated by the same laser beam for viewing its three-dimensional structures. However, advances in image processing technology allow diffraction imaging and three-dimensional feature extraction without necessarily requiring use of the reference beam.

Embodiments according to the present invention will now be discussed with reference to FIGS. 1-21C.

As illustrated in FIG. 1, a microfluidic flow cytometer assembly 10 includes a fluid control unit 100, a coherence distribution detector 130 and a coherence distribution imaging analyzer 140. The fluid control unit 100 includes a core fluid inlet 102, a sheath fluid inlet 104 that provides a core fluid and a sheath fluid, respectively, to a flow path 106 in a microfluidic flow cell 108. The flow cell 108 outputs the core fluid and sheath fluid via a disposal outlet 110. The fluid control unit 100 is configured to form a hydro-dynamically focused flow stream having a core fluid and sheath fluid through the flow path 106 of the flow cell 108. A controller controls the flow of the core fluid and sheath fluid into the inlets 102, 104, respectively. Particles in the core fluid of the hydrodynamically focused flow path 106 pass through the flow cell 108 substantially one at a time. The core fluid includes particles of interest, such as biological cells (including human cells and phytoplankton cells) and other microscopic particles.

The output of a coherent light source, such as a laser beam 120, is configured to illuminate a particle in the inner core fluid of the flow cell 108. An imaging detector or coherence distribution detector 130 is configured to detect a spatially coherent distribution of elasticity scattered light from the particle. An analyzer 140 is configured to extract three-dimensional morphology parameters of the particle from the spatially coherent distribution of the elastically scattered light.

In this configuration, when a particle in the inner core fluid of the flow cell 108 is illuminated, it scatters light in various directions. A complex spatial pattern of the elastically scattered light can be formed that is dependent on the particle's size, shape, intra-particle distribution of refraction index, and/or morphology. According to embodiments of the present invention, the spatial distribution of the elastically scattered light or the diffraction image data can be acquired, for example, by the detector 130, at an appropriate angular range to determine various three dimensional morphological parameters of the particle. For example, the analyzer 140 can use the diffraction image data to extract the volume(s) and refractive index (indices) associated with the structure of the particle, such as a volume and refractive index of the cytoplasm and/or nucleus and/or mitochondrion in a biological cell.

In particular embodiments, the fluid control unit 100 can be a laminar flow controller configured to provide laminar flow at relatively low velocities of 10 mm/s or less, which can allow image acquisition with an exposure time of up to 50 µs with relatively small amounts of displacement (such as less than 0.5 µm) of the particle in the inner core fluid of the flow cell 108. In this configuration, the fluid control unit 100 can provide increased signal to noise ratios for enhanced imaging capabilities, including, e.g., diffraction imaging.

Figure 6:
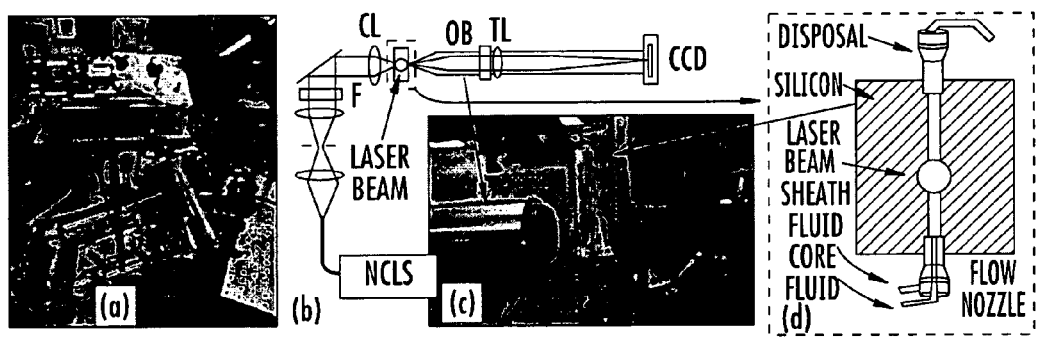
FIG. 6a is a digital image of a fluid control unit according to embodiments of the present invention.
FIG. 6b is a schematic diagram of a cytometer assembly according to embodiments of the present invention.
FIG. 6c is a digital image of a cytometer assembly according to embodiments of the present invention.
FIG. 6d is a schematic diagram of the cytometer assembly of FIG. 6c.

In some embodiments, the microfluidic flow cell 108 can be formed of the material having an index of refraction that is substantially similar to an index of refraction of the sheath fluid in the flow cell 108, such as silicone or other polymer materials. In this configuration, the noise background can be reduced by generally matching the index of refraction of a portion of the flow cell 108 through which the laser 120 is impinged and the fluid flowing inside the flow cell 108. In addition, the flow cell 108 can have at least one planar side, for example, as shown in FIG. 6, such that light from the laser 120 travels substantially perpendicular to the planar side of the flow cell 108 to further reduce noise background due to scattering at the entrance surface of the flow cell 108 and increase the signal to noise ratio.

Figure 2:
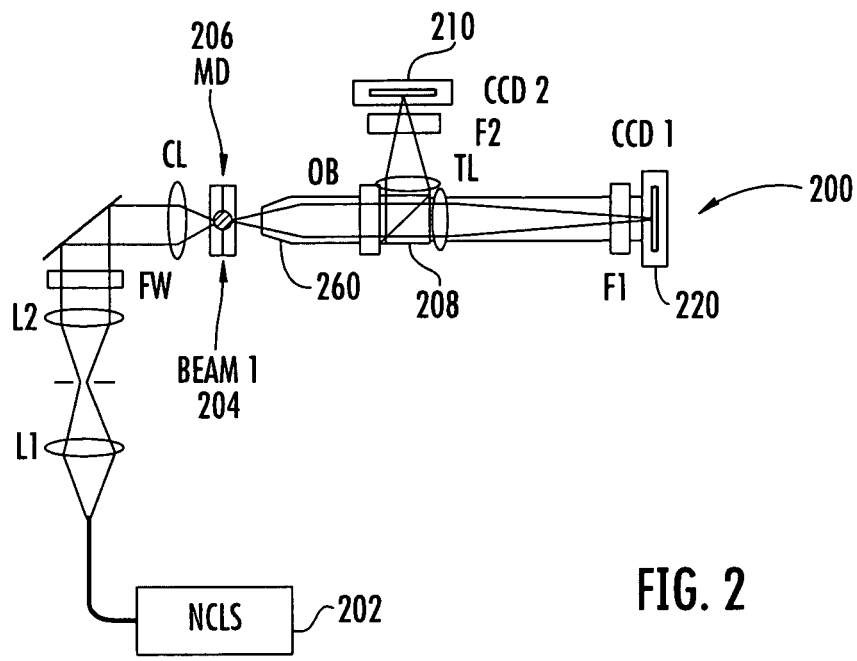
FIG. 2 is a schematic diagram of a cytometer assembly according to other embodiments of the present invention.
Figure 3:
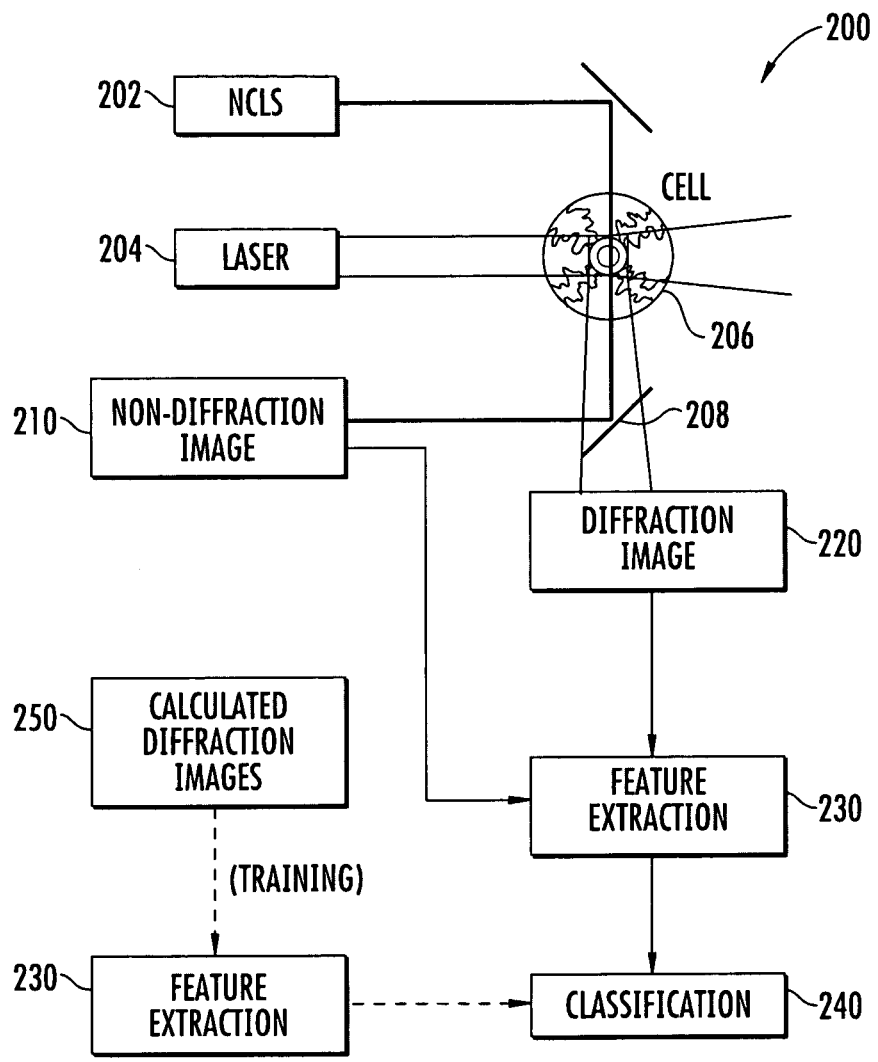
FIG. 3 is a block diagram of a cytometer assembly including diffraction and non-diffraction imaging modules and feature extraction/classification modules according to embodiments of the present invention.

In some embodiments of the current invention as illustrated in FIGS. 2-3, a microfluidic flow cytometer assembly 200 is provided. The assembly 200 includes a non-coherent light source 202, a laser light source 204, a flow cell or microfluidic device 206 (having a cell or other particle flowing therethrough) and a beam splitter 208. Light from a non-coherent light source 202 and the laser light source 204 is impinged on a particle in a microfluidic device 206. Scattered light and fluorescence light are separated when they pass through the beam splitter 208. Elastically scattered light from a particle due to excitation by a laser light beam from the laser light source 204 passes through a filter F1 and is detected by an image detector 220 (e.g., a charge coupled device (CCD1) camera) to acquire diffraction image data, and elastically scattered and/or fluorescent light from the same particle due to the non-coherent light source 202 is acquired by another image detector 210 (e.g., a charge coupled device (CCD2) camera) as bright-field or fluorescent image data depending on the selection of the wavelength filter F2 (shown in FIG. 2). As illustrated in FIG. 2, light from the non-coherent light source 202 can pass through two lenses L1, L2, a filter wheel FW and a condenser lens CL to focus a light beam from the non-coherent light source 202 onto a particle in the microfluidic device 206. Elastically scattered and/or fluorescent light from the particle due to excitation by the non-coherent light source 202 then passes through an objective lens 260 (e.g., an infinity-corrected objective lens) and the beam splitter 208 and through a tube lens TL and filter F2 before being detected by the non-diffraction image detector 210. Elastically scattered light from the laser light source 204 passes through the objective lens 260 and the beam splitter 208 through another tube lens TL and filter F1 before being detected by the diffraction image detector 220.

In this configuration, the detector 220 acquires diffraction images of light scatters near a scattering angle, e.g., of about 90° from the direction of the laser light source 204. The detector 210 can also acquire non-diffraction image data due to excitation by the non-coherent light source 202, such as the non-coherent distribution of elastically scattered light signals for bright-field or dark-field and/or fluorescent signals (for example, using fluorescence staining cells with an appropriate filter F2) for fluorescence imaging data. In some embodiments, the diffraction images and the non-diffraction images can be acquired at substantially the same time and/or combined to provide additional information about particles in the microfluidic device 206. As would be understood by one of skill in the art, the non-diffraction imaging data can provide a replica image of the particle but with details that are limited by the diffraction effect of the residue coherence in the non-coherent light signals of diffraction limit. In some embodiments, the non-diffraction imaging data and the diffraction imaging data can be combined, for example, in an image overlay.

For example, as illustrated in FIG. 3, the non-diffraction imaging data from the image detector 210 and the diffraction imaging data from the detector 220 can be used by a feature extraction module 230. Particles in the microfluidic device 206 can be classified by imaging data analysis using a classification module 240. Various classification techniques can be used, for example, to estimate the volume or other characteristics of features of the particles, such as biological cells. In particular embodiments, calculated diffraction imaging data 250 from particles with a known morphology can be used to "train" various classification techniques, which can be used to extract three dimensional morphological features for particle classification by the classification module 240.

Figure 4A:
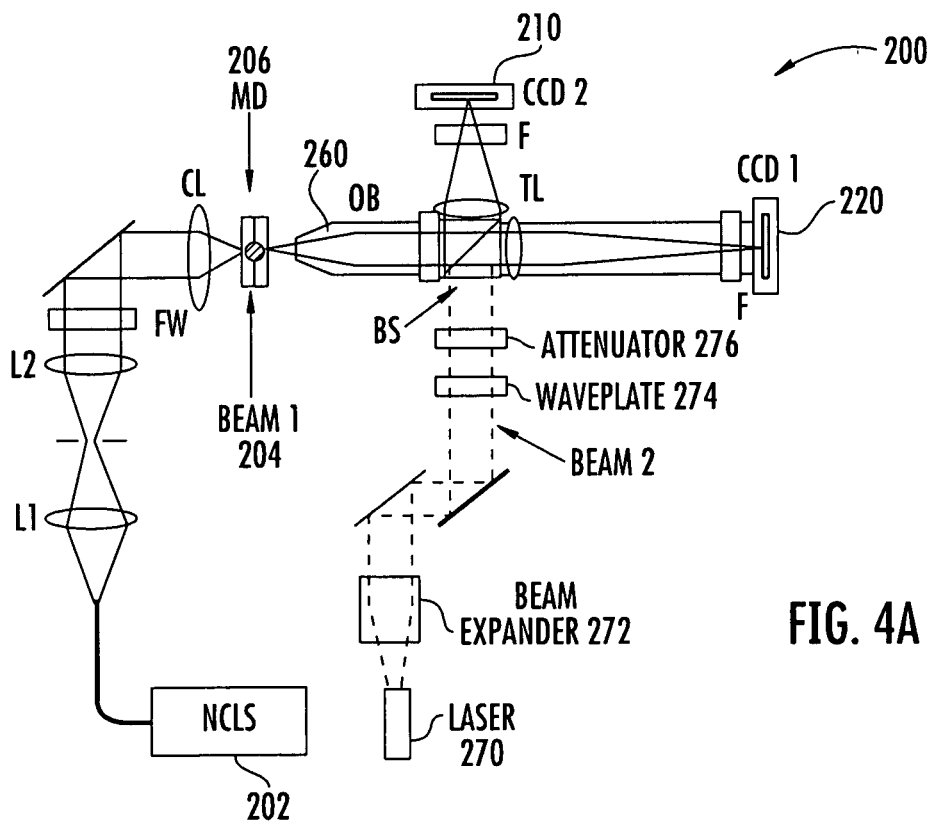
FIG. 4A is a schematic diagram of a cytometer assembly according to additional embodiments of the present invention.
Figure 4B:
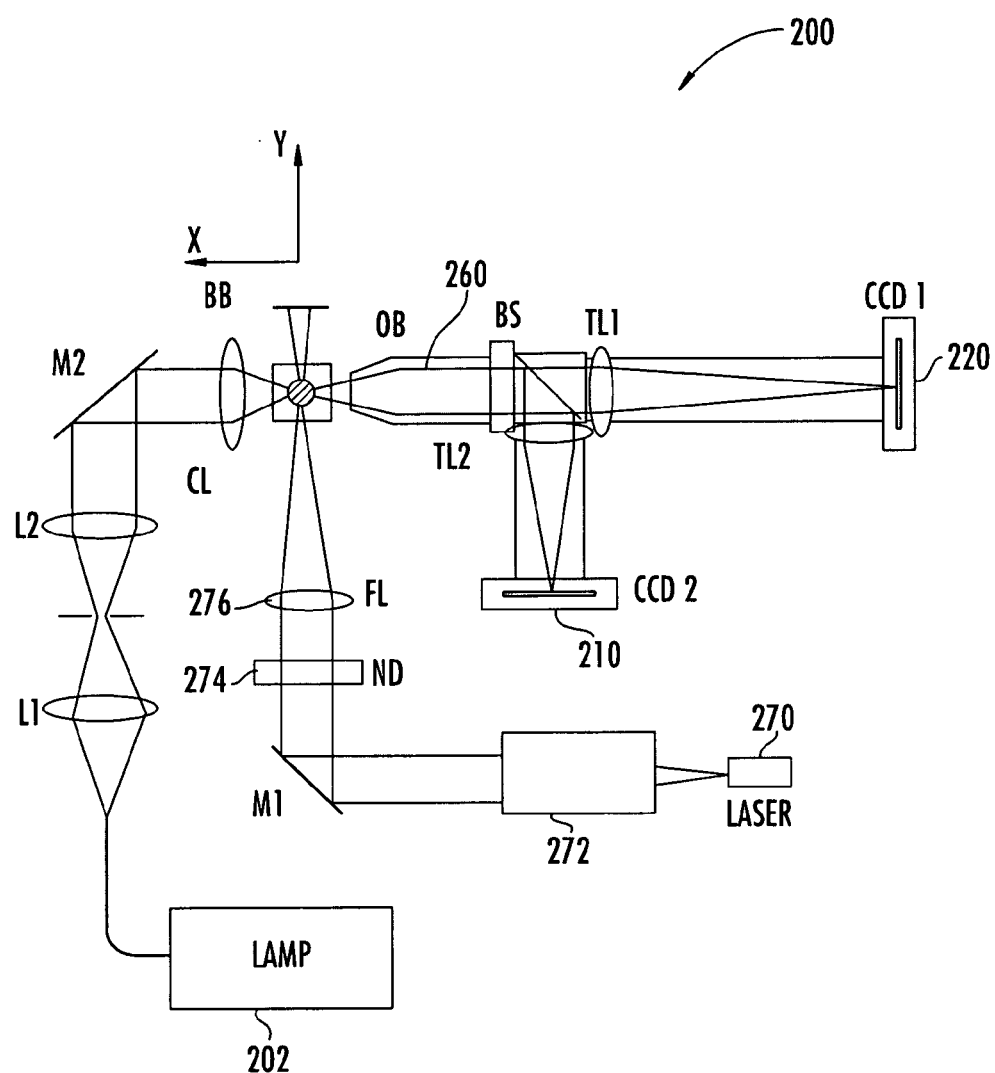
FIG. 4B is a schematic diagram of a cytometer assembly according to additional embodiments of the present invention.

In some embodiments shown in FIGS. 4A-4B, another laser light source 270 can be used to provide an excitation beam for the detector 220 to acquire diffraction images of elastic light scatters in the backscattering directions of near 180°. As illustrated in FIGS. 4A-4B, the laser light source 270 produces a laser beam through a beam expander 272, a wave plate 274, and an attenuator 276 before passing through the beam splitter 208 (which is rotated 90° in comparison to the orientation shown in FIG. 2) prior to scattering light to the cell in the microfluidic device 206 in the backscattering direction.

It should be understood that any suitable light source can be used for the coherent light sources 204, 270 and the non-coherent light source 202. In particular embodiments, the non-coherent light source 202 can be a Kohler illumination system with a 175 W xenon lamp, and the coherent light sources 204, 270 can be provided by the same or different lasers with one or multiple output wavelengths, e.g., between 180 and 3000 nm. Particular wavelength examples that may be suitable include 444 or 532 or 633 nm. The objective lens 260 can be an infinity-corrected objective lens (M Plan Apo HR 50x or 100x, Mitutoyo) with a relatively large numerical aperture and long working distance. By using different distances between the tube lenses TL behind the objective lens 260 and the detectors 210, 220, the diffraction and non-diffraction images can be acquired using the same objective lens 260 as illustrated in FIGS. 2 and 4A-4B. For example, a 50x objective lens may be used. This allows the collection of light scatters within a half angle or width of 48.6° in the air for diffraction image. If the microfluidic device 206 includes a silicone side wall interface through which light from the sources 202, 204 passes, the half angle width may reduce to about 32° due to the light refraction at the air- silicone interface. The detectors 210, 220 can be relatively sensitive EMCCD cameras (DU 885K, Andor technology) of a 1004× 1002 pixels, which may provide a reduced exposure time. Although standard cooled CCD cameras (e.g., Alta U2000) can be used, EMCCD cameras typically have an electron-multiplying mechanism to amplify signals before analog to digital conversion. This feature can allow a three to 10 fold increase in the signal-to-noise ratio for weak light signals on the order of 10 photons per pixel, thus potentially reducing the exposure time from values of about 50 µs to about 10 µs or less to allow higher cell speed in the flow and processing throughput. The EMCCD camera used also has a relatively high pixel readout rate at 35 MHz to achieve a frame transfer rate of 112 frames per second with a 4×4 pixel binning. The dark-current and readout noises of the EMCCD camera can be a relatively low, which can lead to a large dynamic range of the pixel count (e.g., 70 dB) and subsequent 14-bit digitization, which may be useful for more accurate acquisition of diffraction image data. Although specific exemplary angle, pixel numbers, frame speeds, etc. are provided above, it should be understood that any suitable values can be used.

Figure 5:
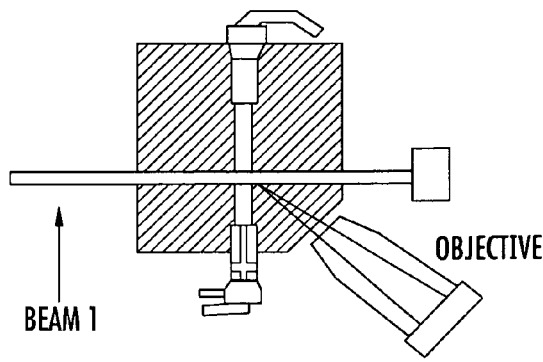
FIG. 5 is a schematic diagram of a cytometer assembly according to embodiments of the present invention.

Accordingly, any suitable cytometer configuration can be used, e.g., to acquire diffraction image data according to embodiments of the present invention. For example, cytometer assemblies according to embodiments of the present invention can be configured to facilitate the acquisition of diffraction images in different angular regions. In addition, a reliable electronic triggering and delay unit can be used for accurately gating the image data acquisition. For example, as shown in FIG. 5, a "shouldered" microfluidic device can be used for acquiring angle-resolved diffraction imaging data centered at 45°.

In some embodiments, the particles are classified by the classification module 204 in FIG. 3 based on the diffraction image data and/or the non-diffraction image data. For example, the particles can be classified by training classification algorithms with a database of diffraction image data and/or the non-diffraction image data of particles of known three-dimensional morphological parameters for various features, which for the case of biological cells can include nuclear volume, nuclear shape, nuclear refractive index heterogeneity, nucleus-to-cytoplasm volume ratio, cell shape, cytoplasm-nucleus refractive index contrast, mitochondria density, mitochondrion-to-cytoplasm index contrast, and mitochondrion-to-nucleus refractive index contrast. Other cell features that can be determined include cell death, binding events, and the like. The training database can be constructed from non-flow-cytometry data by combing the three dimensional morphology features extracted from confocal microscopy imaging data and numerical modeling of elastic light scattering using the rigorous solution of the Maxwell equations. (references: (1) J. Q. Lu, P. Yang, X. H. Hu, "Simulations of Light Scattering from a Biconcave Red Blood Cell Using the FDTD method", Journal of Biomedical Optics, 10(2), 024022 (2005); (2) R. S. Brock, X. H. Hu, D. A. Weidner, J. R. Mourant, J. Q. Lu, "Effect of Detailed Cell Structure on Light Scattering Distribution: FDTD study of a B-cell with 3D Structure Reconstructed from Confocal Images", Journal of Quantitative Spectroscopy & Radiative Transfer, 102, 25-36 (2006)).

In some embodiments, the morphology parameters of a particle can be determined using images acquired at a defocused position with respect to the particle, as described, for example, in Example 4.

Figure 12:
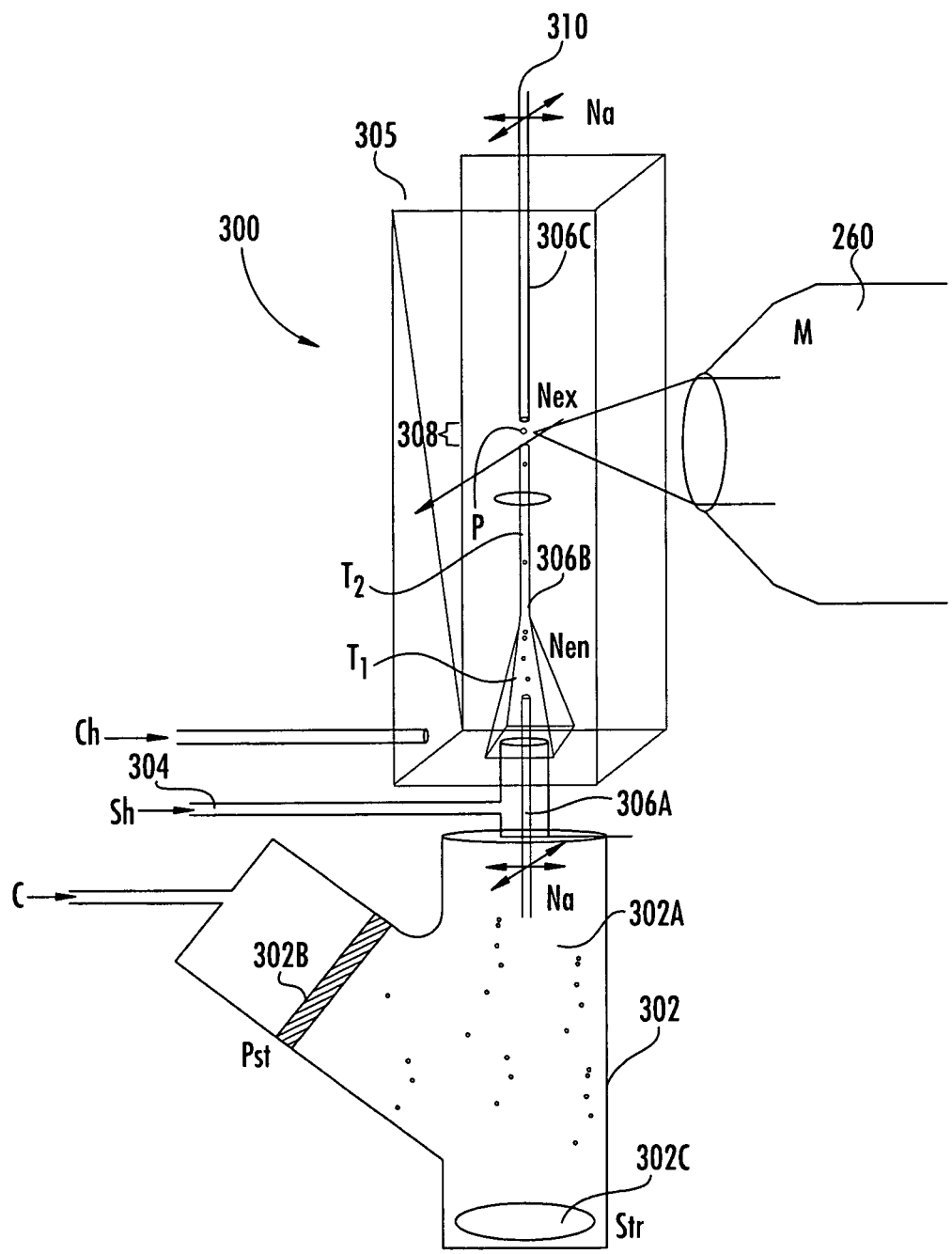
FIG. 12 is a schematic diagram of a cytometer assembly according to some embodiments of the present invention.

Although embodiments according to the present invention are described herein with respect to the microfluidic flow cytometer assembly 10 and the fluid control unit 100 as shown in FIG. 1, it should be understood that other fluid control techniques can be used. For example, fluid control units can be provided in which the fluid is controlled without being fully constrained by a microfluidic device. As shown in FIG. 12, a "jet-in-fluid" based fluid control unit 300 is shown. The fluid control unit 300 includes a core fluid reservoir 302 for containing the core fluid 302A, a sheath fluid inlet 304, and flow path unit 305 having three fluid passages 306A, 306B and 306C. The flow path unit 305 can be a glass cuvette that is filled with a fluid, such as water.

The core fluid reservoir 302 includes a piston 302B for moving the core fluid 302A into the flow path unit 305 such that the core fluid 302A is combined with the sheath fluid from the sheath fluid inlet 304. The core fluid 302A enters a passage 306A, and sheath fluid enters another passage 306B via the inlet 304 such that the core and sheath fluids are combined in the passage 306B. The core fluid reservoir 302 also includes a stirring unit 302C for stirring the core fluid 302A. The flow path unit 305 includes the flow passages 306B and 306C, which have a gap 308 therebetween. The flow rate of the fluid and the passages 306A and 306B can be configured such that the core fluid flows from the passage 306A into the passage 306B to form a laminar flow and then flows through the gap 308 before enters passage 306C followed by an outlet 310. The objective 260 of a camera (e.g., a CCD camera) can be positioned so that the objective 260 can be used to capture an image of a particle P in the flow path unit 305 when the particle P is in the gap 308, and particles P in the core fluid 302A of the hydrodynamically focused flow path pass through the gap 308 substantially one at a time. The core fluid includes particles of interest, such as biological cells (including human cells and phytoplankton cells) and other microscopic particles as described herein.

In this configuration, particle P can be imaged in the gap 308 such that the particle P is substantially free from surrounding materials having mismatched indexes of refraction, such as the solid materials that form the passages 306A, 306B and 306C.

In some embodiments, the passage 306A can be formed of a stainless steel needle, for example, having an inner diameter of about 200 µm and an outside diameter of about 300 µm to guide the core fluid 302A from the reservoir 302 into the passage 306B. The passage 306B can be formed of a square glass tube T1 having a length of about 8 mm on the interior side that connects to a tapered square tube T2 having an interior side length of about 80 µm and an exterior side length of about 230 µm. Inside the tube T2 of the passage 306B, the sheath and core fluids form a laminar flow under appropriate pressure differences from syringe pumps that supply the fluids. The fluids are then collected by the passage 306C such that the particles carried by the laminar flow can remain inside the core fluid in the gap 308 having a diameter as small as about 100 µm. The gap 308 can be about 5 mm. If the fluids in the flow path unit 305 and the passages 306A, 306B and 306C have similar indexes of refraction (such as when the core fluid, the sheath fluid and the fluid in the unit 305 are all water or water-based), index-mismatched interfaces are reduced or eliminated within the field of view (FOV) of the objective 260. For example, the objective 260 can be positioned at least about 13 mm away from the particle P to reduce or eliminate any index-mismatches due to the glass of the unit 305.

It should be understood that any suitable orientation of the flow path unit 305 and objective 260 can be used. For example, the laminar flowing sheath/core fluid in the passage 306B can enter the flow path unit 305 from the top or from a side of the unit 305 rather than from the bottom of the unit 305 as shown in FIG. 12.

Therefore, an image captured through the objective 260 (as described with respect to FIGS. 2, 3, 4A-4B and 5) may have improved image quality due to the reduction in index-mismatched materials in the region adjacent the particle P. When compared to a microfluidic flow cell such as the flow cell 108, the gap 308 contains substantially no optical heterogeneity near the particle P. One or more laser beams can be introduced from the plane side surfaces of the flow path unit 305 to excite the particle P, and the microscope objective 260 of a camera (e.g., a CCD camera) can be used to collect and record scattered light distribution from another side of the flow path unit 305. In some embodiments the objective 260 can be positioned with a field-of-view that is far from the cuvette side surfaces (e.g., about 10-15 mm from the particle P). The jet-in-fluid design of the passages 306B and 306C and the gap 308 can reduce or eliminate the index-mismatched interfaces close to the flowing particle P while provide fluid flow control similar to that of a flow cyometer, e.g., to allow high throughput assay and/or multiple excitation beams.

Additional embodiments according to the present invention will now be discussed with respect to the following non-limiting examples.

EXAMPLE 1

To increase the morphology information that can be retrieved from elastic light scatter due to excitation by a coherent light source, a prototype microfluidic flow cytometer was constructed to test the concept of diffraction image acquisition with a standard cooled CCD imager (Alta U2000). The prototype is shown in FIGS. 6a-6d. A preliminary study of diffraction images with polystyrene microspheres has been performed. The prototype can have the specifications as set forth in Table 1.

TABLE 1

The expected specifications of the proposed dual-image microfluidic flow cytometer

| | |
|---|---|
| Adjustable flow speed | 0.01~0.50 m/s |
| Adjustable core fluid diameter | 20~150 µm |
| Half-width of angular region for diffraction image* | 32° |
| Center of angular region for diffraction image | 5°, 45°-135°, 180° |
| Lateral resolution of the non-diffraction image* | 0.4 µm |
| Field of view of non-diffraction image* | 320 µm × 240 µm |
| CCD Camera exposure time | 10-10,000 µs |
| Image frame transfer rate (251 × 250 pixels per image frame) | 112 frames/s |
| SNR of CCD image^ | ~3000 |

*Assuming and infinity-corrected objectives lens of 50x, working distance = 5.2 mm, NA = 0.75 at λ = 633 nm.
^SNR = signal-to-noise ratio of EMCCD camera: signal = well depth, noise = dark current noise + readout noise.

As illustrated in FIG. 6a, two glass syringes with precisely and independently controlled moving pistons form a flow control unit using gears and stepping motors. The syringes function as the reservoirs of sheath and core fluids to generate a laminar flow in a silicone microfluidic device by applying an appropriate pressure by the moving pistons. Silicone polymer of a refractive index 1.41 at 633 nm is hardened in a mold with long glass fibers to make microfluidic devices with a smooth-walled microchannel with diameter variable between 20 and 200 µm. The microchannel is connected to the flow control unit with a standard flow cytometer nozzle to allow a stable laminar flow with a length of about 80 mm. Several microfluidic device designs have been tested to establish laminar flows with different core fluid diameter and flow speed. Compared to the conventional flow cytometer, the silicone polymer based microfluidic device has several features: very long distance of laminar flow (80 mm vs 10 mm), low core flow speed (0.01 m/s to 1 m/s vs 10 m/s) and nearly matched refractive indices between the sheath fluid and surrounding medium (0.02 or less between glycerol/water mixer of sheath fluid and silicone vs 0.2 between water and glass). The last two features may result in the achievement of relatively slow exposure times of up to 50 μs with a standard cooled CCD camera on the slow-moving particle (which moves 0.2 μm at a speed of 0.01 m/s) and/or reducing the noise background due to the scattered light at the flow-silicone interface.

To evaluate the microfluidic flow cytometer, an imaging system was designed to acquire diffraction images of microspheres of 25 μm diameter interrogated by a 633 nm laser beam. An infinity-corrected objective lens (Plan Apo 50×, Mitutoyo) was used to acquire diffraction images by a cooled CCD camera. A Kohler illumination with a xenon arc lamp provides a non-coherent light source (NCLS) for acquisition of bright-field images for system alignment. The diffraction images of light scatters were acquired with the NCLS blocked. With the objective of a 13 mm working distance and 0.55 numerical aperture (NA), the acquired scatter image corresponds to the angular ranges of scatter of $\theta_s$ and $\phi_s$ (see FIG. 7 for definitions) between 70° and 110° from the incident direction of laser beam. The Mie theory of light scattering by spheres was used to obtain the calculated diffraction image in FIG. 8b with the refractive indices of polystyrene and water (as the host medium) at 633 nm for comparison to the measured one shown in FIG. 8a. The field-of-view of the calculated image was determined from the angular range defined by the objectives lens's numerical aperture (NA) and working distance. It can be noted that the measured and calculated images agree well on the characteristic oscillatory pattern of light intensity. Improvement of the imaging optics may further reduce the background noise.

EXAMPLE 2

Coherent scattering of a monochromatic light beam occurs as a dominant form of interaction when the refractive index n becomes heterogeneous, $n(r,\lambda)$, where r is the position vector inside a particle and $\lambda$ is the wavelength for both incident and scattered light, shown schematically in FIG. 9. The scattered fields lead to the spatially coherent and characteristic scatter distributions which can be acquired as diffraction (spatial) or speckle (spatial and temporal) images. With accurate wave models based on the solution of the Maxwell equations or wave model trained pattern recognition software, it is possible to extract intra-particle refractive index distribution and thus three-dimensional morphology information of the scatterer or cells from the elastic light scatter distribution or diffraction image data. The intra-particle index distribution of $n(r,\lambda)$ correlates with cell's morphology. (Ref: R. Baer, "Phase contrast and interference microscopy in cytology," in *Physical Techniques in Biological Research*, edited by A. W. Pollister (Academic Press, New York, 1966), Vol. 3, pp. Ch. 1.) Most of biological cells have size parameters $\alpha$ ($=2\pi a/\lambda$) ranging between 1 and 100 for UV/visible and near-infrared light with 2a as the mean diameter (see FIG. 9). Accurate modeling of light scattering requires numerical calculation of the scattered electromagnetic fields using realistic three-dimensional cell structures that can be acquired with, for example, the confocal imaging technique. Recent progress in numerical modeling has led to new tools to study the correlation between cell morphology and angle-resolved light scatter distribution or diffraction image. These include the development of parallel codes based on the finite-difference-time-domain (FDTD) and discrete dipole approximation (DDA) algorithms on low-cost parallel computing clusters. (Ref: J. Q. Lu, P. Yang, X. H Hu, "Simulations of Light Scattering from a Biconcave Red Blood Cell Using the FDTD method," *J. Biomed. Opt.*, 10, 024022 (2005); R. S. Brock, X. H. Hu, P. Yang, J. Q. Lu, "Evaluation of a parallel FDTD code and application to modeling of light scattering by deformed red blood cells," *Opt. Express*, 13, 5279-5292 (2005); M. A. Yurkin, K. A. Semyanov, P. A. Tarasov, A. V. Chernyshev, A. G. Hoekstra, V. P. Maltsev, "Experimental and theoretical study of light scattering by individual mature red blood cells by use of scanning flow cytometry and a discrete dipole approximation," *Appl Opt*, 44, 5249-56 (2005); M. A. Yurkin, A. G. Hoekstra, R. S. Brock, J. Q. Lu, "Systematic comparison of the discrete dipole approximation and the finite difference time domain method for large dielectric scatterers," *Opt. Express*, 15, 17902-17911 (2007)). In addition, methods to construct three dimensional structure of cells based on their confocal images for FDTD or DDA simulations have been developed. (Ref: R. S. Brock, X. H Hu, D. A. Weidner, J. R. Mourant, J. Q. Lu, "Effect of Detailed Cell Structure on Light Scattering Distribution: FDTD study of a B-cell with 3D Structure Constructed from Confocal Images," *J. Quant. Spectrosc. Radiat. Transfer*, 102, 25-36 (2006); H. R. Hurwitz, J. Hozier, T. LeBien, J. Minowada, K. Gajl-Peczalska, I. Kubonishi, I. Kersey, "Characterization of a leukemic cell line of the pre-B phenotype," *Int. J. Cancer*, 23, 174-180 (1979).)

A parallel FDTD code to simulate the spatially coherent distribution of elastic light scattering by B-lymphocyte cell line NALM-6 cells has been developed that can used, combined with the three dimensional morphology of these cells, to construct a database to train the software classification module. The three dimensional structures of stained NALM-6 cells were constructed from their confocal images with a nuclear dye (Syto 61, Invitrogen). FIG. 10 is a table including the three dimensional structural parameters of seven NALM-6 cells. By importing the three dimensional structures into the FDTD code, various Mueller matrix elements were obtained, of which the element $S_{11}$ represents the scattered light intensity normalized by the unpolarized incident beam intensity. The following were assumed in the simulations: (1) both the nucleus and the cytoplasm regions are homogeneous; (2) the incident wavelength $\lambda_O=1$ μm in vacuum; (3) the cytoplasm has a complex refractive index of $n_c=1.3675+i1.0\times10^{-5}$ while nuclear index is either $n_n=1.42$ or 1.46 (Ref: J. R. Mourant, M. Canpolat, C. Brocker, O. Esponda-Ramos, T. M. Johnson, A. Matanock, K. Stetter, J. P. Freyer, "Light scattering from cells: the contribution of the nucleus and the effects of proliferative status," J Biomed Opt, 5, 131-7 (2000)); (4) each cell is suspended in a host medium with a refractive index of $n_h=1.35$. The FDTD grid cell size was set at $\Delta x=\lambda/20$ with $\lambda=\lambda_0/n_h$. To study the dependence of light scatter on cell orientation, 12 sets of orientation angles of the cell $(\theta_0, \phi O)$ were selected, covering the $4\pi$ solid angle uniformly.

Figure 11:
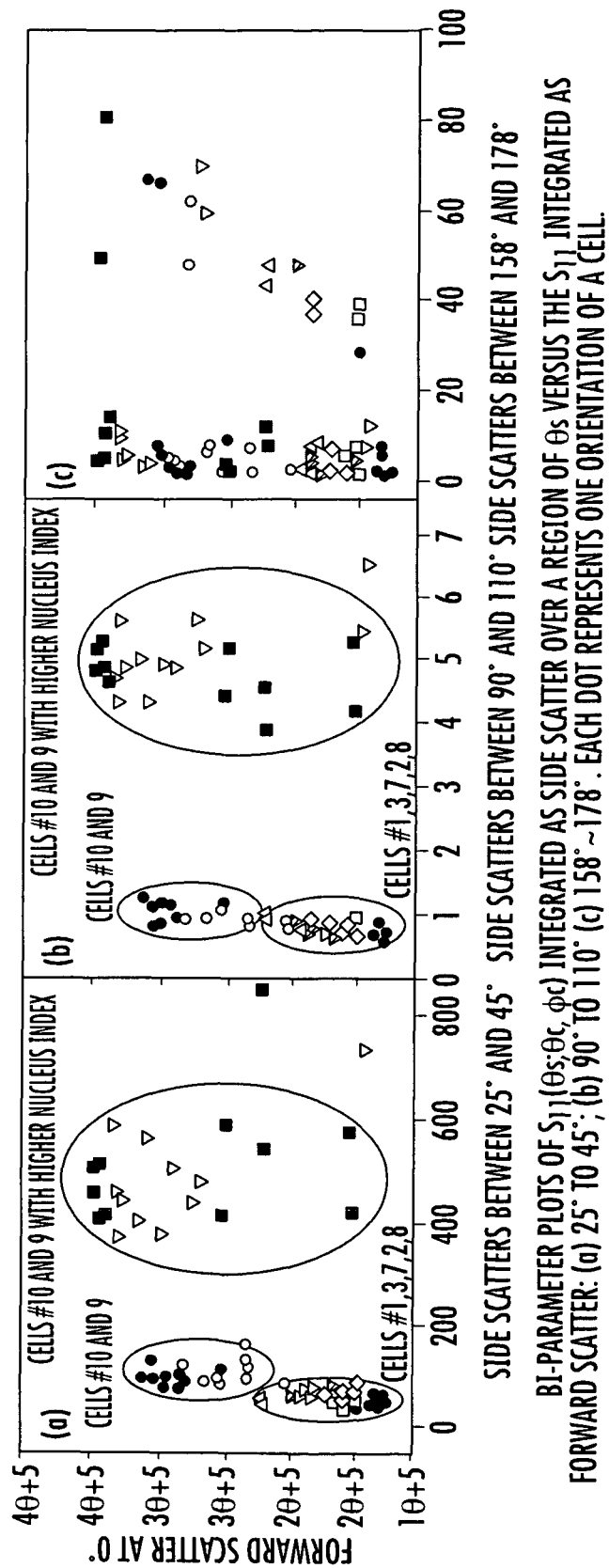
FIG. 11 is a graph of 9 NALM-6 cells distributed in the 2D feature subspaces defined by the light scatter of element S11 at $\theta_s$=0° versus its integrated value in different angular range of $\theta_s$ as side scatters.

FIG. 11 presents three plots of 9 NALM-6 cells distributed in the two dimensional feature subspaces defined by the light scatter of element $S_{11}$ at the scattering polar angle $\theta_s=0°$ versus its integrated value in different angular range of $\theta_s$ as side scatters. These are based on the seven cells shown in FIG. 10 with 2 additional cells obtained by assigning high nuclear index for the #9 and #10 cell. The dots representing the same cell are for different orientations. It can be first observed that the dots of the same cell with different orientations tend to cluster together. This demonstrates that the light scatter distribution is insensitive to the cell orientation. The forward scatter intensity does not exhibit a simple linear relation as often expected by the conventional view. Furthermore, as shown in the first two plots of FIG. 10, the cluster of cells in their dividing stages with splitting nuclei (cells #10 and #9) are separated from the cluster of the cells with regular shaped nucleus (cells #1, 3, 7, 2, and 8) and the cluster with higher nuclear index of refraction. These results show that detailed analysis of angle-resolved scatter distribution or diffraction image data can provide rich information on cell morphology and index distribution, and an accurate modeling tool can produce a training database for development of a robust pattern recognition software for extracting 3 D morphology features rapidly.

EXAMPLE 3

Forty cultured NALM-6 cells in different cell cycles are selected as a cell model to establish a training database for cell classification. The cells are stained and imaged with a confocal microscope (LSM 510, Zeiss). The three dimensional structures will be constructed for two purposes. First, these structures will be imported into our FDTD code for simulations of angle-resolved elastic light scatter from the cell excited by a coherent light beam. Second, these structures will be analyzed to define multiple classes of morphology features as the basis for development of the pattern recognition software for cell classification. Light scattering by a single biological cell can be modeled as a plane wave incident on a dielectric scatterer in a host medium. To account for the polarization change associated with scattered light, a framework of Stokes vectors is adopted for the incident and scattered light fields and a Mueller matrix for the cell.

Figure 7:
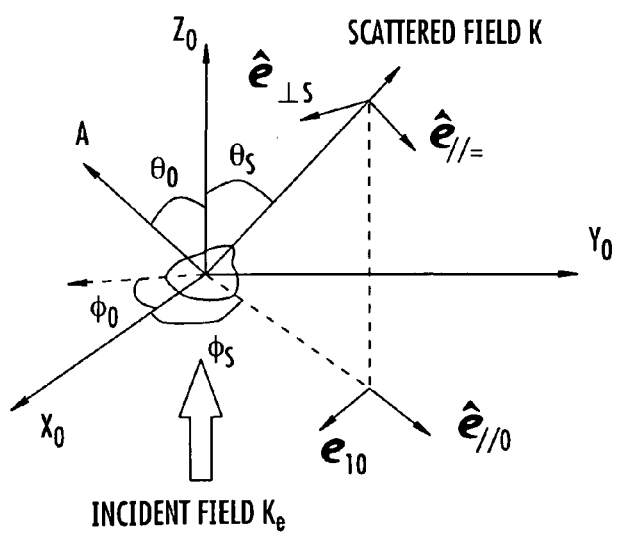
FIG. 7 is a schematic diagram of the incident field and scattering field for a particle according to embodiments of the present invention.

The incident light is represented by its electromagnetic fields of $(E_0, H_0)$ with E representing the electric field and H the magnetic field with a wave vector $k_0$ while the scattered light by $(E_s, H_s)$ with k ($|k_0|=|k|=2\pi/\lambda$), as shown in FIG. 7. The host medium, such as the laminar fluids, is characterized by a refractive index $n_h$ and the cell by a spatially variant refractive index, $n(r, \lambda)$, corresponding to its three dimensional structure. Because of the linear relation between the incident and scattering fields, a complex 2×2 amplitude matrix describes the effect of cell with the fields separated into components parallel and perpendicular to the scattering plane defined by k and $k_o$ $$\begin{pmatrix} E_{\|S} \\ E_{\perp S} \end{pmatrix} = \frac{e^{ikr+ikz}}{-ikr} \begin{pmatrix} S_2 & S_3 \\ S_4 & S_1 \end{pmatrix} \begin{pmatrix} E_{\|O} \\ E_{\perp 0} \end{pmatrix} \quad (1)$$

Since the 2×2 matrix elements are complex and related to field amplitudes, a real 4×4 Mueller matrix S that relates directly to the measurable intensity signals of light can be defined. The Mueller matrix is defined as $$\begin{pmatrix} I_S \\ Q_S \\ U_S \\ V_S \end{pmatrix} = \frac{1}{k^2 r^2} \begin{pmatrix} S_{11} & S_{12} & S_{13} & S_{14} \\ S_{21} & S_{22} & S_{23} & S_{24} \\ S_{31} & S_{32} & S_{33} & S_{34} \\ S_{41} & S_{42} & S_{43} & S_{44} \end{pmatrix} \begin{pmatrix} I_O \\ Q_O \\ U_O \\ V_O \end{pmatrix}, \quad (2)$$

where I, Q, U, V are the Stokes parameters of the incident light (with subscript 0) and the scattered light (with subscript s). All matrix elements are function of scatter angles of $(\theta_s, \phi_s)$ and cell orientation angles of $(\theta_0, \phi_0)$. The element $S_{11}$ yields the probability of an unpolarized incident light being scattered into the direction of $\theta_s$ and $\phi_s$ while other elements provide information on scattered light with different polarization states.

Given the incident fields (E, H) at $\lambda$ and $n(r, \lambda)$, based on the three dimensional structure of the cell with assigned indices for different intracellular components, the Mueller matrix elements $S_{ij}$ can be calculated using the numerical method of FDTD or DDA. (Ref: J. Q. Lu, P. Yang, X. H Hu, "Simulations of Light Scattering from a Biconcave Red Blood Cell Using the FDTD method," *J. Biomed. Opt.*, 10, 024022 (2005); R. S. Brock, X. H. Hu, P. Yang, J. Q. Lu, "Evaluation of a parallel FDTD code and application to modeling of light scattering by deformed red blood cells," *Opt. Express*, 13, 5279-5292 (2005); R. S. Brock, X. H Hu, D. A. Weidner, J. R. Mourant, J. Q. Lu, "Effect of Detailed Cell Structure on Light Scattering Distribution: FDTD study of a B-cell with 3D Structure Constructed from Confocal Images," *J. Quant. Spectrosc. Radiat. Transfer*, 102, 25-36 (2006); H. Ding, J. Q. Lu, R. S. Brock, T. J. McConnell, J. F. Ojeda, K. M. Jacobs, X. H. Hu, "Angle-resolved Mueller Matrix Study of Light Scattering by B-Cells at Three Wavelengths of 442, 633 and 850 nm," *J. Biomed. Opt.*, 12, 034032 (2007)). It has recently been shown that the DDA algorithm can be 10 to 100-fold faster than FDTD algorithm for large cells such as the NAM-6. (Ref: M. A. Yurkin, A. G. Hoekstra, R. S. Brock, J. Q. Lu, "Systematic comparison of the discrete dipole approximation and the finite difference time domain method for large dielectric scatterers," *Opt. Express*, 15, 17902-17911 (2007)). The database for training software classification module includes, but not limited to, the diffraction images of $S_{11}$, $S_{12}$, $S_{22}$ and $S_{34}$ calculated from the NALM-6 cells excited by coherent laser beams at, e.g., three wavelengths of 444, 532 and 633 nm and the three dimensional structure of these cells constructed from their confocal images.

Accurate calculation of diffraction images, which is $S_{ij}(\theta, \phi)$ projected to the CCD sensor plane of (x, y), may be acquired using a realistic three dimensional structures of the cell as a scatterer. The three dimensional structures of cells can be constructed from their confocal image stacks with index values assigned, and the data can be imported into a simulation such as the FDTD or DDA software code. For example, a red nucleic acid dye (Syto 61, Invitrogen) is used to stain the cells before confocal imaging. Histogram analysis of the confocal image pixels separates them into three groups according to their red fluorescence emission intensities: those pixels in the host medium of PBS (after washing), pixels in cytoplasm and those inside the nuclear membrane. By tracing the boundaries between pixel groups in each confocal image, contours are obtained for the nuclear and cytoplasmic membranes. These contours are connected through different image planes along the z-axis of the confocal microscope, the three dimensional structures of cytoplasm and nucleus are constructed and different values of refractive index are assigned for $n(r, \lambda)$. The values of $n(r, \lambda)$ are based on fitting the Mueller matrix elements $S_{ij}$ to experimental data. (Ref: A. Zharinov, P. Tarasov, A. Shvalov, K. Semyanov, D. R. van Bockstaele, V. P. Maltsev, "A study of light scattering of mononuclear blood cells with scanning flow cytometry," *JQSRT*, 102, 121-128 (2006); H. Ding, J. Q. Lu, R. S. Brock, T. J. McConnell, J. F. Ojeda, K. M. Jacobs, X. H. Hu, "Angle-resolved Mueller Matrix Study of Light Scattering by B-Cells at Three Wavelengths of 442, 633 and 850 nm," *J. Biomed. Opt.*, 12, 034032 (2007)).

Recently, the Mueller matrix elements $S_{ij}$ have been measured for both human promyelocytic leukemia NALM-6 and HL-60 cell suspensions using a goniometer configuration. For some elements, such as $S_{12}$ and $S_{34}$, experimental data indicated large differences between these two cell types even though their 3D structures exhibit high similarity. Test results demonstrate that the introduction of mitochondria may account for the observed difference in $S_{ij}$. To develop a robust pattern recognition software, the three dimensional structure construction of the NAM-6 cells can be enhanced by using two different dyes (Syto 61 and MitoTracker Orage, Invitrogen or other combination) to co-stain the nucleus and mitochondria with different emission wavelength bands before imaging. This allows inclusion of both components in the three dimensional structures for accurate simulation of diffraction images.

While the numerical modeling tools discussed above may be highly accurate, the intensive computing can take 1 or 2 hours to calculate one diffraction image from an imported cell structure on a 16-node computing clusters. Inverse determination of morphology structures and refractive indices from measured diffraction image may be a very slow process and not practical for analyzing large cell populations. Accordingly, a pattern recognition or particle classification software module trained by a database established using the techniques discussed above can be used to rapidly extract multiple three dimensional morphology features and refractive indices from the dual image data (/. e., non-diffraction image data and diffraction image data) for particle classification. The pattern recognition or particle classification software can include two parts. The first part extracts the orientation and two dimensional morphology parameters as the fiduciary marks from the non-diffraction image of bright-field or fluorescence and molecular features for stained cells excited by the non-coherent light source, and the second part extracts three dimensional morphology features from the particle excited by the coherent light source to build a classification vector with up to 20 components for cell classification. Each morphology component of the classification vector is related to an aspect of the three dimensional morphology of the flown particle, which in the cases of biological cells includes nuclear volume, nuclear shape, nuclear index heterogeneity, nucleus-to-cytoplasm volume ratio, cell shape, cytoplasm-nucleus index contrast, mitochondria density, mitochondrion-to- cytoplasm index contrast, and mitochondrion-to-nucleus index contrast. The fiduciary marks from the first part of the classification software module will be used in the second part as the constraints to reduce the probability of misclassification. The second part of the classification software includes two components: (1) a feature extractor to extract three dimensional morphology feature from a diffraction image; and (2) a classifier to generate a classification vector. A feature extractor selects multiple three dimensional morphology features from diffraction image data for classification of a large cell population. One exemplary design of a feature extractor for the classification software discussed below is based on the Support Vector Machines (SVM) algorithm (Ref: I. Guyon, J. Weston, S. Barnhill, V. Vapnik, "Gene selection for cancer classification using support vector machines," Mack Learn. , 46, 389-422 (2002)); however, other algorithms such as neural networks and statistical pattern recognition can be used. SVM is a supervised leaning tool that allows classification of image data in an image space defined by a kernel function. It can solve a classification problem with an optimization process to identify a maximum margin hyperplane that separates the image data from a training database into multiple instances or classes. The hyperplane is based on a set of boundary training instances or support vectors. The optimization problem can be formulated by an objective function as the metric to measure the progress, which also allows treatment of non-separable data by penalizing misclassifications. Once the hyperplane is established with the training data, the NALM-6 cell image data acquired will be classified according to locations in the high-dimension space in relation to the hyperplane. SVM has been successfully used for multi-class classification of complex biological systems such as the classification of multiple tumor types based on genes. SVM often performs better than other methods for classification problems in an image space of high dimension with very few samples per class.

The classification/pattern recognition software will generate a classification vector with multiple components based on the three dimensional morphology and molecular features as discussed above. For each component, an SVM will be built to compute its morphology-related value. In the following, the procedures related to extraction of a classification vector component associated with the nuclear volume are described, which serve as an example to illustrate the proposed SVM based methodology. Other components associated with three dimensional morphology features may be treated similarly, including additional morphology features not mentioned below. The procedures described below are designed for generating a component associated with the nuclear volume from a diffraction image data of NALM-6 cells. Other cell types can be treated by the same approach using corresponding training database.

1. Nuclear volume scaling. The output of an SVM for the component determined from a diffraction image is not nuclear volume Vn: rather, it is a classification value (CR). For a CR scale of 10, CR=0.1, 0.2, 0.3 . . . , 1.0, the range of Vn is divided into 10 value sections. If the minimal and maximal values of Vn for the cells in the training database are 200 $\mu m^3$ and 2000 $\mu m^3$, respectively, then cells having Vn≤200 $\mu m^3$ are classified as the instances of CR=0.1, and those with Vn≥2000 $\mu m^3$ are classified as CR=1.0 while rest of the cells are classified as instances of CR values equally partitioned between 0.1 and 1.0 according to Vn. Development of other classification vector components is similar.

2. Labeling training database. Each diffraction image in the training database is labeled with a classification vector based on their morphology parameters extracted from the 3D structure constructed from the confocal images. A software tool can be developed to automatically label each image. The tool will perform statistical analysis to obtain the range value of each parameter from the database to determine appropriate instances of the component values and automatically map an absolute parameter value to a CR value for the component.

3. Image vector generation in an image space. Each diffraction image of light scatter $S_{ij}(\theta_s, \phi_s)$ (256×256 pixels) forms an image vector of 256×256 elements in an image space defined by an appropriate kernel function. In the simplest case, an image space can be formed by the pixel coordinates, x and y as projected from the scattering angles $\theta_s$ and $\phi_s$ to the CCD sensor plane, with a dimension of 65,536. In this image space, the image vector is located by its pixels of (k, z), where k=256x'+y' with (x', y') as the renormalized pixel coordinates between 1 and 256 and 0≤z≤1 as the normalized value of $S_{ij}$.

4. Classification algorithm. The study of SVM based algorithm begins by projecting all image vectors in the image space with the selected kernel function for diffraction images in the training database of NALM-6 cells. The SVM algorithm will then proceed to establish a hyperplane through a learning process that separates or discriminates image vectors into classes with appropriate class labels as defined in Procedure 2 above. After completion of the classification for the diffraction images from the training database, the SVM algorithm will be applied to classify new image vectors according to its location relative to the established hyperplane in the image space.

5. Generation of classification vector. Various tools can be used to develop an effective and efficient SVM classifier for each component associated with a three dimensional morphology feature. The results of classification on each of the three dimensional morphology features will be combined with molecular features, available for stained cells; to generate a classification vector for each cell in the studied population. Different kernel functions can be developed to achieve increased or optimized classification for each of the classification vector component. A kernel function is used to transform the diffraction images from the original CCD sensor plane coordinates of (x, y) to another space as the image space. A good kernel function can improve classification with an image space in which all image vectors aggregate in separate clusters for different classes. Possible kernel functions, including polynomial or Gaussian function and wavelet transform, will be studied to evaluate their performance.

The SVM based method described herein employs an one-versus-all (OVA) scheme in combing multiple binary classifiers to make a decision for classification. In the example of nuclear volume discussed above, 10 binary classifiers will be constructed in relation to the support vectors defined by the 3D structure in the training database. For each image vector, its distances to all support vectors in the image space are calculated so that a confidence measure (CM) of the binary classifier to a particular support vector can be obtained. The CM value ranges between −1.0 and 1.0 which correspond to largest and smallest distances to the support vector, respectively, and each CM indicates if the imaging vector belongs to a class (CM>0) or not (CM<0). The OVA scheme refers to the classification rule of assigning a cell to the class whose CM value is the largest among all the CM values. Table 2 below shows 3 examples of classification based on this scheme.

analysis of large populations in a multi-dimensional feature space previously not available. The benefits of three dimensional morphology features can be manifest through the example of cell death study. Cell death, defined as the irreversible loss of plasma membrane integrity, can occur in numerous ways according to different morphology and molecular characteristics. The three major types of cell death in mammalian cells are necrosis, apoptosis and autophagy. Apoptosis and autophagy are different forms of programmed death triggered by intrinsic pathways: apoptosis is characterized mainly by changes in nuclear morphology followed by blebbing of the plasma membrane and overall cell shrinkage while autophagy is characterized by a massive accumulation of two-membrane vacuoles in the cytoplasm followed by fusing with lysosomes. In contrast, necrosis is a response to external and incidental stimuli by cytoplasmic swelling and dilation of cytoplasmic organelles. As a high throughput instrument, flow cytometry techniques as described herein may be capable of quantitative assay of death mode and associated time courses in large and heterogeneous cell populations by extraction of three dimensional morphology and molecular parameters.

EXAMPLE 4

Figures 13A, 13B, 13C:
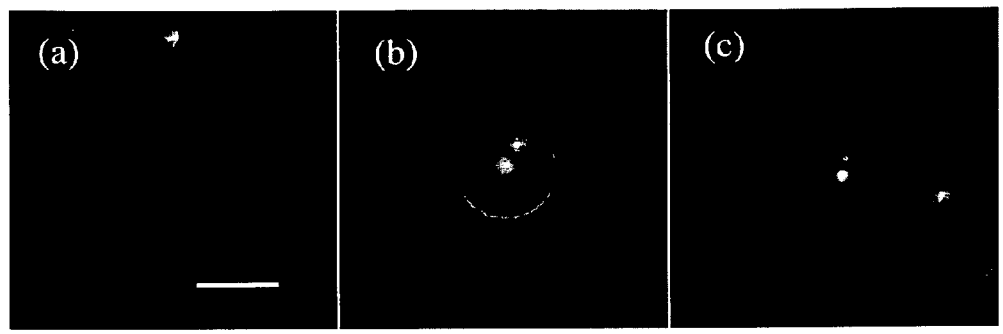
FIGS. 13A-13C are bright-field digital images acquired with the objective positioned at x=0 of a sphere of d=9.6 µm (FIG. 13A), a sphere of d=25 µm (FIG. 13B) and a B16/GPR4 cell with Bar=20 µm (FIG. 13C).

The effect of the objective location on the diffraction imaging has been investigated using the system of FIG. 4B. Once the specimen had been located, the objective 260 was first aligned into the focused position under white light illumination. This position was employed for later image acquisition as the reference position or x=0. FIGS. 13A-13C presents three examples of these non-coherent images acquired under the white light illumination at x=0.

Figure 14:
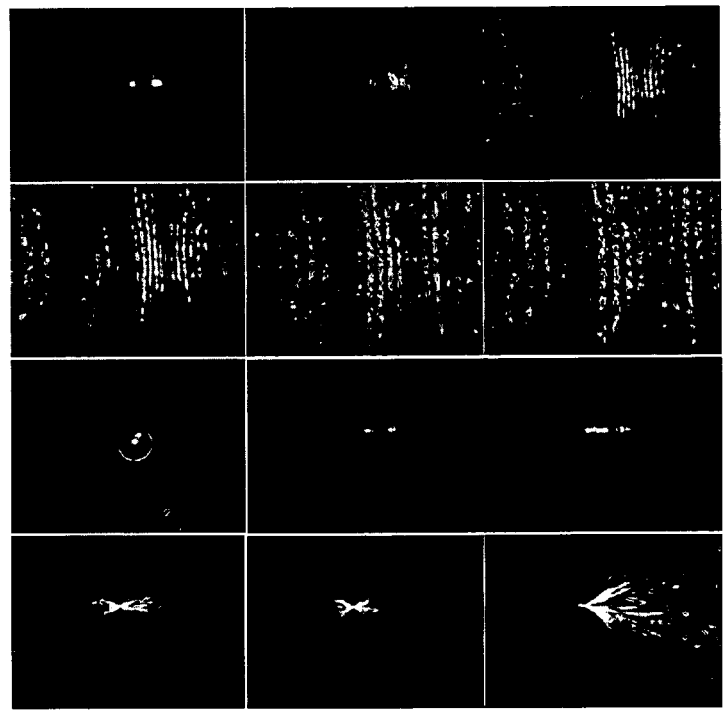
FIG. 14 illustrates digital diffraction images and one bright-field image acquired with non-coherent white light (third row, first column) of a polystyrene sphere of 25 µm in diameter (embedded in gel). The diffraction images were acquired with a laser beam of λ=532 nm in wavelength and the objective at different x positions. From left to right, first row: x=0 µm, 100 µm, 200 µm; second row: x=300 µm, 400 µm, 500 µm; third row: x=0 µm (bright field image), −100 µm, −200 µm; fourth row: x=−300 µm, −400 µm, −500 µm.
Figure 15:
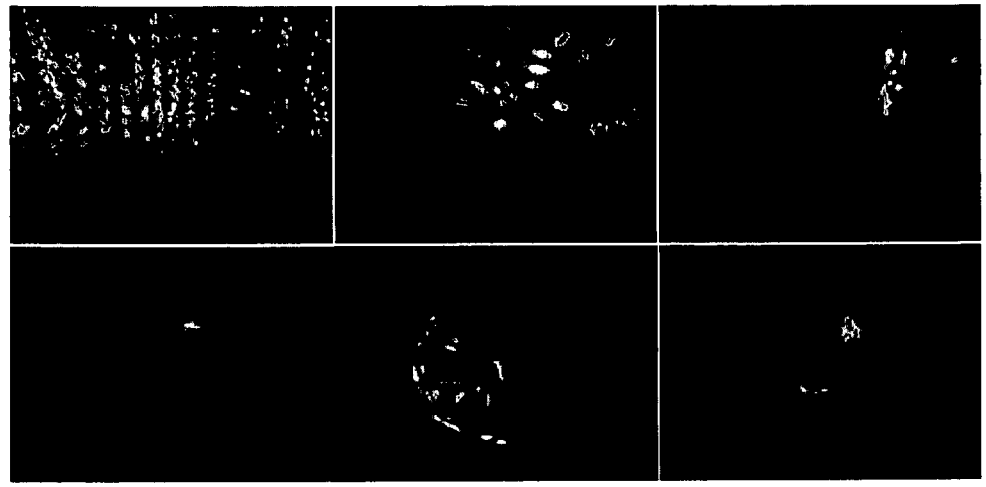
FIG. 15 illustrates digital diffraction images of a polystyrene sphere of 9.6 µm in diameter in the left column and two melanoma cells that are embedded in gel: B16/vector (cell #1) in the middle column and B16/GPR4 (cell #3) in the right column. The first row is imaged at x=200 µm, and the second row is imaged at x=−200 µm.

After the system alignment, the laser beam was introduced for diffraction imaging and the imaging system was translated from the reference position of x=0 and diffraction images were taken at each stop with exposure times ranging from 50 μs to 3 s. The direction of x>0 refers to moving the objective towards the specimen. FIG. 14 displays a set of diffraction

TABLE 2

The CM value table and OVA classification rule

| CR scale | 0.1 | 0.2 | 0.3 | 0.4 | 0.5 | 0.6 | 0.7 | 0.8 | 0.9 | 1.0 | class |
|---|---|---|---|---|---|---|---|---|---|---|---|
| Cell image 1 | 0.8 | 0.5 | 0.3 | 0.4 | −0.1 | −0.2 | −0.3 | 0.1 | 0.2 | −0.3 | 0.1 |
| Cell image 2 | 0.1 | −0.5 | 0.2 | 0.3 | −0.1 | −0.2 | 0.3 | 0.7 | 0.2 | −0.4 | 0.8 |
| Cell image 3 | −0.7 | −0.4 | −0.7 | −0.4 | 0.4 | −0.9 | −0.3 | 0.1 | 0.1 | −0.3 | 0.5 |

Additionally, acquisition signals and raw results such as images may be represented following the Flow Cytometry Standard (FCS) data file format, which was adopted by the International Society for Analytical Cytology (ISAC), to promote cytometer data exchange and interoperability. A software utility for representing and displaying data based on XML format or other suitable formats can be used.

Embodiments according to the present invention can acquire diffraction and non-diffraction imaging data of particles excited with coherent and non-coherent light sources by elastic light scatters and/or fluorescence signals using microfluidic flow cytometry. This can allow the extraction of three dimensional morphological features simultaneously with the molecular features from the fluorescence signals from stained particles and thus can open the possibility of single-particle images acquired at x between −500 μm and +500 μm from a sphere of 25 μm in diameter. These image data exhibit two features. First the images acquired at x>0 present the characteristic vertical fringe pattern one expects from the Mie theory of light scattering by single spheres. Further, and counterintuitively, the images acquired at increasing x values exhibit expanded fringes in the FOV of the camera. Second the images acquired at x<0 contain fringe patterns that are largely independent of the specimen's structure as the objective is moved away from the specimen.

In addition to the sphere of 25 μm in diameter, imaging of polystyrene spheres of 9.6 μm in diameter and 4 melanoma cells using the same sequence of translating the objective at different x positions was carried out. The dependence of the diffraction images exhibit similar features as discussed above on the two sides of x=0. After analysis of the sphere image data, it was determined that the diffraction images acquired at x=200 μm correlate strongly with the particle morphology and examples of these images are presented in FIG. 15 together with those acquired at x=−200 μm as comparison.

Figure 16:
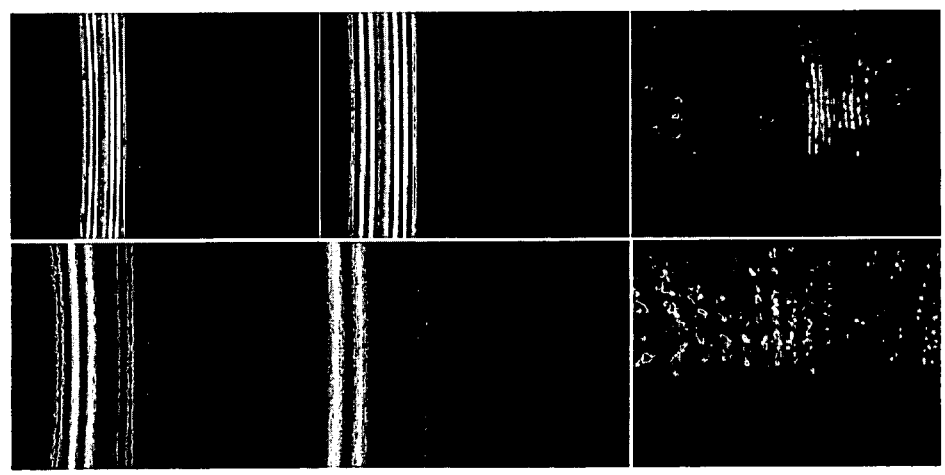
FIG. 16 illustrates digital projection images calculated from angle-resolved scattered light distribution by the Mie theory with Θ=24° for images in the left column and Θ=16° in the middle column. The images in the right column are measured diffraction images of the spheres embedded in gel with x=200 µm with a diameter of 25 µm in the first row and 9.6 µm in the second row.

To understand these diffraction image data, the angle-resolved scattered light distribution based on the Mie theory (see C. F. Bohren and D. R. Huffman, Absorption and Scattering of Light by Small Particles, p. 447 (Wiley, New York 1983)) was calculated and projected the results on a y-z plane as calculated diffraction images without consideration of the objective and tube lens. The refractive indices of 1.59 and 1.40 were used for the sphere and host medium of gel (comprising water, glycerol, and hydroxyethyl cellulose), respectively, for the wavelength of $\lambda$=532 nm. Different values of the angular distance $\Theta$ were used in the calculated diffraction images, which corresponds to the half-width angular distance of FOV along the horizontal direction or y-axis. The calculated and measured diffraction images are shown in FIG. 16 for spheres of the two different diameters.

In obtaining the calculated images, the microscope objective was not considered and the only variable was the angular distance $\Theta$, with decreasing $\Theta$ corresponding to expanded fringes in FOV. Comparing of the calculated images at different $\Theta$ with the measured images acquired at x=200 μm, as shown in FIG. 16, shows that a best fit is achieved with $\Theta$=16° if the number of fringes in FOV are used as the criterion. Note that the half cone angle $\theta$ corresponding to the objective placed at the focused position (x=0) is 23° based on the objective's NA (=0.55) and the refractive index of the gel (n=1.40). The result of $\Theta$=16° for the calculated image is comparable to the diffraction image acquired with the objective moved towards the sphere from x=0 by 200 μm, which is unexpected and should be due to the defocused objective. The fringes in the calculated images do not curl near the edges of FOV as those in the measured one which may be attributed to the effect of the objective as well.

The morphological changes induced in the B16F10 cells were examined to determine if these cells can be used as a model for study of the correlation between diffraction images and 3D morphological features. It was observed that the expression of the G protein-coupled receptor, GPR4, in B16F10 cells increased the formation of dendrites and led to changes in morphology. Furthermore, it has been found that GPR4 expression increased melanin content by 4 fold by direct measurement of melanin concentration with a spectrophotometer due to the increased production of melanin particles, which are markers of melanocyte differentiation. An assay of 10,000 cells has been performed with a conventional flow cytometer (FACScan, Becton Dickinson) for each of the two cell types and the plots of light scatter are presented in FIGS. 17A-17B. From these data, one can observe that the mean value of the foward scatters by the B16/vector cells (mean value=391) are slightly larger than that by the B16/GPR4 cells (mean value=375) while the relation in side scatters is reversed (228 vs 414).

To quantitatively investigate the morphological changes, 3D reconstruction of melanoma cells has been performed with developed software through confocal imaging. The pixels in the confocal image stacks were first sorted into three groups: cytoplasm, nucleus and mitochondria according to the intensity and wavelength of fluorescence emission. Then the contours of related organelles between neighbouring slices were connected for 3D structure and volume calculation. One example of 3D structure for a B16/GPR4 cell is presented in FIG. 18 in two sectional views. Five cells from each of the two cell types were randomly selected to acquire confocal image stacks for 3D reconstruction. The extracted volume data are listed in Table 3 below. Further study of the molecular mechanisms and functional significance of GPR4-induced morphological change and melanin production and differentiation in B16F10 cells are currently under investigation.

TABLE 3

The volume parameters of B16F10 cells (μm$^3$)

|  | B16/GPR4 | B16/vector |
|---|---|---|
| nuclear* | 1103 ± 307 | 1164 ± 533 |
| mitochondria* | 206 ± 63 | 297 ± 107 |
| cell*# | 3586 ± 892 | 4910 ± 2170 |
| N/C^ | 31% | 24% |
| Mean radius (μm) | 9.50 | 10.5 |

*in the form of mean ± std with 5 cells in each group.
equal to the volume sum of cytoplasm, nucleus and mitochondria.
^mean volume ratio of nucleus-to-cell.

It is interesting to note that the cytoplasm volumes of the two cell types appear to be different while the volumes of the nucleus and mitochondria between the two types are close in values. The fact that B16/vector cells have larger cytoplasm volume may be used to explain the feature revealed by the plots of light scatters in FIGS. 17A-17B, which can be interpreted as the B16/vector cells having larger cell volume and less intracellular heterogeneity. Furthermore, the variation in cytoplasm volume, induced by the GPR4 receptor, may suggest a significant difference between the cytoskeletons of these cells which can have important consequences in cells' ability for adhesion and migration. While a conventional flow cytometer can be used to acquire light scattering data as shown in FIGS. 17A-17B, one can clearly see that these data provide very limited quantitative information on 3D morphology. In contrast, the diffraction images presented herein demonstrate large difference between spheres of different sizes and spheres and cells of similar sizes and thus can be used to extract 3D morphological features as we discussed in the introduction. A study of different B16F10 cell populations with a diffraction imaging flow cytometer and comparison with FDTD numerical modelling may be conducted.

Figure 19:
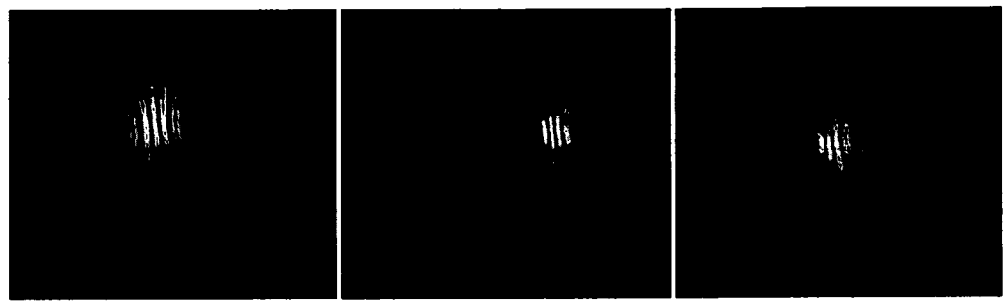
FIG. 19 illustrates digital images of 9.6 µm diameter spheres in 532 nm light with a flow speed of between about 1.6 mm/s and 1.8 mm/s and an exposure rate of 50 µs.
Figure 20:
FIG. 20 illustrates digital images of 9.6 µm diameter spheres in 532 nm light with a flow speed of about 12 mm/s.
Figure 21A:
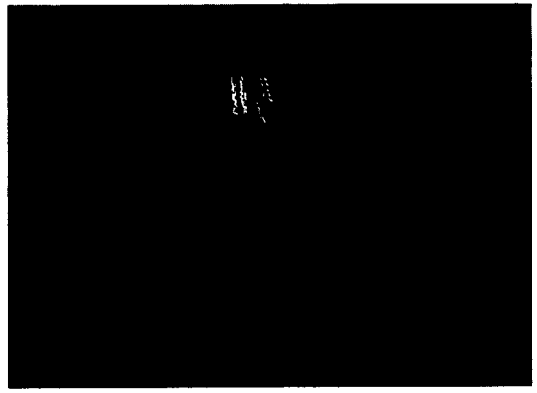
FIG. 21A is a digital image of a 5.2 µm diameter spheres with a flow speed of between about 4.7 mm/s.
Figure 21B:
FIG. 21B is a digital image of a 9.6 µm diameter sphere with a flow speed of about 12 mm/s.
Figure 21C:
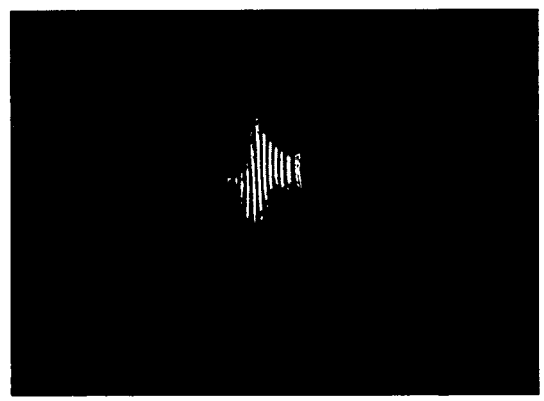
FIG. 21C is a digital image of a 25 µm diameter sphere with a flow speed of about 7 mm/s.

It should be understood that the techniques described herein can be used with respect to particles in a fluid control unit, such as the fluid control unit of FIG. 12. FIGS. 19, 20 and 21A-21C are digital images of spheres taken using the fluid control unit of FIG. 12. In particular, FIG. 19 illustrates digital images of 9.6 μm diameter spheres in 532 nm light with a flow speed of between about 1.6 mm/s and 1.8 mm/s and an exposure of 50 μs. FIG. 20 illustrates digital images of 9.6 μdiameter spheres in 532 nm light with a flow speed of about 12 mm/s and an exposure of 50 μs. FIG. 21A is a digital image of a 5.2 μm diameter spheres with a flow speed of between about 4.7 mm/s. FIG. 21B is a digital image of a 9.6 μm diameter sphere with a flow speed of about 12 mm/s. FIG. 21C is a digital image of a 25 μm diameter sphere with a flow speed of about 7 mm/s.

One potential disadvantage of the current technology based on integrated light signals lies in its potentially limited capability in extracting morphological features which carry rich information on cells. Experimental results are presented related to the diffraction imaging of single specimen embedded in gel with a microscope objective. The results show that diffraction images acquired with an objective correlate strong correlation with the 3D morphology of the specimen if these images are taken at a defocused position towards the specimen. The 3D structures of tumorigenically transformed B16F10 melanoma cells have been investigated, and it has been established that these cells can be used as a model for study of 3D morphology with the diffraction imaging method. With the flow-in-fluid techniques described herein, the method of diffraction imaging with a microscope objective can be implemented in a flow cytometer to acquire rapidly image data for extraction of 3D morphological features, for example, at a rate of $10^2$ cells per second.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A flow cytometer assembly, comprising:
a fluid controller configured to form a hydrodynamically focused flow stream, the stream including an outer sheath fluid and an inner core fluid;
a coherent light source configured to illuminate a particle in the inner core fluid;
a detector configured to detect a spatially coherent distribution of elastically scattered light from the particle excited by the coherent light source; and
an analyzing module configured to extract a three-dimensional morphology parameter of the particle from a spatially coherent distribution of the elastically scattered light.

2. The cytometer assembly of claim 1, wherein the fluid controller comprises a first fluid passageway, a second fluid passageway and a fluid-filled gap between the first and second fluid passageway, wherein the detector is configure to detect the spatially coherent distribution of elastically scattered light from the particle excited by the coherent light source when the particle is in the gap between the first and second fluid passageways.

3. The cytometer assembly of claim 1, wherein the detector is further configured to provide diffraction image data of the particle comprising the spatially coherent distribution of the elastically scattered light.

4. The cytometer assembly of claim 3, further comprising a non-coherent light source configured to illuminate the particle and a detector configured to detect non-coherent image data comprising bright-field and/or dark-field and/or fluorescence signals from the particle excited by the non-coherent light source.

5. The cytometer assembly of claim 4, wherein the analyzing module is configured to combine the diffraction image data and the non-coherent image data.

6. The cytometer assembly of claim 3, wherein the analyzing module is configured to classify the particles based on the coherence distribution of the elastically scattered light.

7. The cytometer assembly of claim 3, wherein the analyzing module is configured to extract a morphology feature of a structure of the particle based on the diffraction image data.

8. The cytometer assembly of claim 7, wherein the diffraction image data comprises image data from a defocused position with respect to the particle.

9. The cytometer assembly of claim 7, wherein the structure of the particle comprises a volume and refractive index of the cytoplasm and/or nucleus and/or mitochondrion in a biological cell.

10. The cytometer assembly of claim 1, wherein the fluid controller is configured to form a laminar flow stream.

11. The cytometer assembly of claim 1, wherein the fluid controller comprises a flow cell having an index of refraction that is substantially similar to an index of refraction of the fluid sheath.

12. The cytometer assembly of claim 11, wherein the flow cell has at least one generally planar side.

13. The cytometer assembly of claim 1, wherein the detector is configured to detect light scattered within an angle range centered at an angle offset from a direction of light propagation from the coherent light source.

14. The cytometer assembly of claim 13, wherein the angle is about 90 degrees.

15. The cytometer assembly of claim 1, wherein the analyzing module is configured to extract the three-dimensional morphology parameters based on a database of calculated and/or experimentally determined cell images.

16. A method of analyzing particles in a flow cytometer to determine three-dimensional morphology parameters, the method comprising:
forming a hydrodynamically focused flow stream, the stream including an outer sheath fluid and an inner core fluid;
illuminating a particle in the inner core fluid with a coherent light source;
detecting elastically scattered light from the particle excited by the coherent light source; and
extracting a three-dimensional morphology parameter of the particle from a spatially coherent distribution of the elastically scattered light.

17. The method of claim 16, wherein forming a hydrodynamically focused flow stream comprises passing the flow stream through a fluid-filled gap in a fluid passageway, and the spatially coherent distribution of elastically scattered light from the particle excited by the coherent light source is detected when the particle is in the gap.

18. The method of claim 16, further comprising providing diffraction image data of the particle comprising the spatially coherent distribution of the elastically scattered light resulting from excitation by the coherent light source.

19. The method of claim 18, further comprising illuminating the particle with a non-coherent light source and detecting non-coherent image data comprising elastically scattered and/or fluorescence signals resulting from excitation by the non-coherent light source.

20. The method of claim 19, further comprising combining the diffraction image data and the non-coherent image data.

21. The method of claim 18, further comprising classifying the particles based on the coherence distribution of the elastically scattered light.

22. The method of claim 18, further comprising identifying a volume and refractive index of a structure of the particle based on the diffraction image data.

23. The method of claim 22, wherein the structure of the particle comprises a volume and refractive index of the cytoplasm and/or nucleus and/or mitochondrion in a biological cell.

24. The method of claim 16, wherein forming a hydrodynamically focused flow stream comprises forming a hydrodynamically focused laminar flow stream.

25. The method of claim 16, further comprising providing a flow cell having an index of refraction that is substantially similar to an index of refraction of the sheath fluid.

26. The method of claim 25, wherein the flow cell has at least one generally planar side.

27. The method of claim 16, wherein the detected light is scattered within an angular range centered at an angle offset from a direction of light propagation from the coherent light source.

28. The method of claim 27, wherein the angle is about 90 degrees.

29. The method of claim 16, wherein the three-dimensional morphology parameter is extracted based on a database of calculated and/or experimentally determined cell images.

30. The method of claim 16, wherein the detected light is detected from a defocused position with respect to the particle.

31. A computer program product for analyzing particles in a flow cytometer to determine three-dimensional morphology parameters, the flow cytometer having a hydrodynamically focused flow stream including an outer sheath fluid and an inner core fluid, a coherent light source configured to illuminate a particle, and a detector for detecting a coherent distribution of elastically scattered light from the particle excited by the coherent light source, the computer program product comprising a computer usable storage medium having computer-readable program code embodied in the medium, the computer-readable program code comprising:

computer-readable program code that is configured to receive diffraction image data comprising a spatially coherent distribution of elastically scattered light from the flow cytometer; and computer-readable program code that is configured to extract a three-dimensional morphology parameter of the particle from the spatially coherent distribution of the elastically scattered light.

32. The computer program product of claim 31, further comprising computer-readable program code that is configured to receive non-coherent image data from the flow cytometer, the non-coherent image data comprising bright-field and/or dark-field image data of elastically scattered light signals and/or fluorescence image data from the particle resulting from excitation by the non-coherent light source.

33. The computer program product of claim 32, further comprising computer-readable program code that is configured to combine the diffraction image data and the non-coherent image data for a particle in the flow cytometer.

34. The computer program product of claim 33, further comprising computer-readable program code that is configured to classify the particles based on the coherence distribution of the scattered light.

35. The computer program product of claim 31, further comprising computer-readable program code that is configured to identify a volume and refractive index of a structure of the particle based on the diffraction image data.

36. The computer program product of claim 34, wherein the structure of the particle comprises a volume and refractive index of the cytoplasm and/or nucleus and/or mitochondrion in a biological cell.

37. The computer program product of claim 31, wherein the three-dimensional morphology parameter is extracted based on a database of calculated and/or experimentally determined cell images.

* * * * *